(12) United States Patent
Hirshberg

(10) Patent No.: US 10,625,029 B2
(45) Date of Patent: Apr. 21, 2020

(54) NEEDLE SYSTEM

(71) Applicant: David Hirshberg, Haifa (IL)

(72) Inventor: David Hirshberg, Haifa (IL)

(*) Notice: Subject to any disclaimer, the term of this patent is extended or adjusted under 35 U.S.C. 154(b) by 718 days.

(21) Appl. No.: 15/296,068

(22) Filed: Oct. 18, 2016

(65) Prior Publication Data
US 2017/0095621 A1 Apr. 6, 2017

Related U.S. Application Data

(63) Continuation of application No. 14/326,537, filed on Jul. 9, 2014, now Pat. No. 9,931,478, which is a
(Continued)

(51) Int. Cl.
| | |
|---|---|
| *A61M 5/32* | (2006.01) |
| *A61M 31/00* | (2006.01) |
| *A61N 1/05* | (2006.01) |
| *A61B 5/15* | (2006.01) |
| *A61B 8/12* | (2006.01) |
| *A61M 5/50* | (2006.01) |
| *A61B 5/145* | (2006.01) |
| *A61N 1/36* | (2006.01) |
| *A61B 17/3205* | (2006.01) |
| *A61M 5/20* | (2006.01) |

(Continued)

(52) U.S. Cl.
CPC ......... *A61M 5/3297* (2013.01); *A61B 5/145* (2013.01); *A61B 5/14532* (2013.01); *A61B 5/15* (2013.01); *A61B 5/150984* (2013.01); *A61B 5/6848* (2013.01); *A61B 8/12* (2013.01); *A61B 17/32053* (2013.01); *A61M 5/20* (2013.01); *A61M 5/5086* (2013.01); *A61M 37/0015* (2013.01); *A61N 1/0502* (2013.01); *A61N 1/3605* (2013.01); *A61N 1/36017* (2013.01); *A61B 2017/00017* (2013.01); *A61B 2017/00345* (2013.01); *A61B 2017/00752* (2013.01); *A61B 2017/00761* (2013.01); *A61M 2005/206* (2013.01); *A61M 2037/003* (2013.01); *A61M 2037/0023* (2013.01); *A61M 2037/0053* (2013.01); *A61M 2037/0061* (2013.01)

(58) Field of Classification Search
CPC ...... A61B 17/320068; A61B 17/22004; A61B 2017/00345
See application file for complete search history.

(56) References Cited

U.S. PATENT DOCUMENTS

| | | | |
|---|---|---|---|
| 5,976,088 A * | 11/1999 | Urbano | A61B 8/543 600/443 |
| 2005/0228313 A1* | 10/2005 | Kaler | A61B 5/14514 600/583 |

(Continued)

*Primary Examiner* — Matthew F Desanto

(57) ABSTRACT

A needle system for penetrating to or passing thought an object or an organ comprising a semiconductor die, one or more needles, wherein the needles move relative to the die using one or more actuators. The actuators are controlled by a controller wherein the controller instruct the needle to penetrate into or to pass through and/or retract from the object or organ. The needle system is used among other treatments for drug delivery, blood extraction, blood analysis, glucose measurements, blood measurements, nerve system stimulus treatment, hair removal, skin lesions coloring or removal or tattoo painting or removal.

20 Claims, 11 Drawing Sheets

Related U.S. Application Data continuation-in-part of application No. 13/426,684, filed on Mar. 22, 2012, now Pat. No. 9,409,006.

(60) Provisional application No. 61/473,779, filed on Apr. 10, 2011.

(51) Int. Cl.
*A61M 37/00* (2006.01)
*A61B 5/00* (2006.01)
*A61B 17/00* (2006.01)

(56) References Cited

U.S. PATENT DOCUMENTS

| | | | |
|---|---|---|---|
| 2010/0121307 A1* | 5/2010 | Lockard | A61M 37/0015 604/506 |
| 2013/0023769 A1* | 1/2013 | Tsai | A61B 5/6848 600/461 |
| 2013/0144149 A1* | 6/2013 | Luo | A61B 5/685 600/407 |

* cited by examiner

NEEDLE SYSTEM

RELATED APPLICATION/S

This application is a continuation-in-part (CIP) of U.S. patent application Ser. No. 14/326,537 filed Jul. 9, 2014, which is a continuation-in-part (CIP) of U.S. patent application Ser. No. 13/426,684 filed Mar. 22, 2012, which claims priority under 35 U.S.C. § 119(e) of U.S. provisional patent application 61/473,779 filed Apr. 10, 2011. The contents of the above documents are incorporated by reference as if fully set forth herein.

FIELD AND BACKGROUND OF THE INVENTION

The present invention, in some embodiments thereof, relates to array of needles that penetrate objects or organs, and more particularly, but not exclusively, to medical treatments for humans with array of needles.

Needles are thin objects, optionally hallow, with sharp tip in its end to allow penetration into or passage through an object or organ. Needles have many usages. It is used in sewing, in crafting for making small holes, in research, especially in biology, and in medicine. In medicine, needles are used to inject fluid into or extract fluid from the body as well as in other treatments, such as stimulating treatments, like acupuncture, or for monitoring treatment, like brain activity probing and monitoring.

One of the most popular type of needle is a hypodermic needle that is configured to penetrate the skin. In some applications, the needle is injecting fluid to or extracting fluid from the intercellular fluid and in other applications extracting blood or injection drugs to or from a blood vassal.

Typically today, hypodermic needle is made of stainless-steel and the diameter of the needle is between 0.2 mm, i.e., 200 micron, to 5 mm. In recent years, needles with a thin diameters are made also from other materials, such as silicon. These needles are produced using semiconductors manufacturing processes and fabrication facilities.

SUMMARY OF THE INVENTION

According to an aspect of some embodiments of the present invention there is provided needle system that penetrates objects or organs, in general and more particularly, but not exclusively, needle system that is used for medical treatments for humans.

According to an aspect of some embodiments of the present invention there is provided an apparatus for piercing an object comprising:
(a) a semiconductor die; (b) one or more needles; and (c) one or more actuators, wherein the actuators are attached to the die substrate and to the needles, the actuators move the needles relative to the die plan, and the needles are configured to pierce the object.

According to some embodiments of the invention the one or more needles are configured to slide over the die plane.

According to some embodiments of the invention the one or more needles moves out of die plane.

According to some embodiments of the invention the one or more actuators are thermal actuators.

According to some embodiments of the invention the one or more actuators are piezoelectric actuators.

According to some embodiments of the invention the one or more needles are used as ultrasound transducers to generate an image of the object.

According to some embodiments of the invention the one or more needles have mechanical support to hold the needle and to allow sliding only to a desired direction.

According to some embodiments of the invention the apparatus further comprises ratchet mechanism.

According to some embodiments of the invention the apparatus further comprises force transmission mechanism.

According to some embodiments of the invention the apparatus further comprises needle sliding support mechanism.

According to some embodiments of the invention the apparatus further comprises needle friction reduction mechanism.

According to some embodiments of the invention the apparatus further comprises piezoelectric actuator comprising one or more piezoelectric crystals.

According to some embodiments of the invention the apparatus further comprises 2D array of out of die plane movable needle.

According to an aspect of some embodiments of the present invention there is provided a needle system comprising a controller and one or more apparatuses for piercing an object comprising: (a) a semiconductor die; (b) one or more needles; and (c) one or more actuators, wherein the actuators are attached to the die substrate and to the needles, the actuators move the needles relative to the die plan, and the needles are configured to pierce the object.

According to some embodiments of the invention, the object treated by the needle system is a human organ and the system is used for hypodermal treatment.

According to some embodiments of the invention, the needle system is further used for any one of or any combination of (1) drug delivery; (2) blood extraction; (3) blood analysis; (4) glucose measurements; (5) blood measurements; (6) nerve stimulation; (7) hair removal; and (8) skin lesions removal.

According to some embodiments of the invention, the object is an article of manufacturing and the system is used for manipulating or piercing the object during the process of the manufacturing.

According to some embodiments of the invention, the object is a lab object under test or a biological organ and the system is used for testing or measuring or manipulating the lab object under test or the biological organ.

According to some embodiments of the invention,
The needle system of claim 8, wherein the needle system further comprising one or more actuator drivers.

According to some embodiments of the invention,
The needle system of claim 8, wherein the needle system further comprising any one of or any combination of (1) injection subsystem, (2) injection tanks, (3) injection ports, (4) suction subsystem, (5) suction tanks, (6) suction ports, (7) monitoring subsystem, (8) imaging monitoring subsystem, (9) stimulation subsystem, (10) power subsystem, (11) communication subsystem.

According to some embodiments of the invention, the needle system further comprises an adhesive patch package and a die, wherein the die plane is in parallel with the adhesive patch package.

According to some embodiments of the invention, the needle system further comprises a plurality of dies, wherein the plurality of dies plane is perpendicular to the adhesive patch package and the plurality of dies plane comprise needles configured to penetrate the object.

According to some embodiments of the invention, a portion of the needles are penetrating the object in tilted way to provide anchoring effect between the needle system and the object.

According to some embodiments of the invention, the needle system is attached to a foot toe, a needle is targeted to an artery provided blood to a nail bed located under the nail of said foot toe, said nail contains a fungus infection and the needle system injects anti-fungal drug into said artery.

According to some embodiments of the invention, the needle system is attached over the skin in proximity to a target blood vessel, a needle is targeted to suck blood from said blood stream and the blood is stored in a tank reside in the needle system.

According to some embodiments of the invention, the blood is monitored by the needle system or monitored by another apparatus.

According to some embodiments of the invention, the needle is targeted to a nerve organ or fiber and the needle system stimulate the nerve organ or fiber with the needle.

According to some embodiments of the invention, the needle stimulate the nerve organ or fiber by electric stimuli, heat stimuli, material injection stimuli or vibration stimuli.

According to an aspect of some embodiments of the present invention there is provided a method for hypodermic treatment comprising the steps of:
(a) attaching to a skin a device comprising one or more dies comprising: one or more needles; and one or more actuators, wherein the actuators are attached to the die substrate and to the needles, the actuators move the needles relative to the die plan, and the needles are configured to pierce the object; (b) penetrating the skin by moving the needles into the skin; (c) performing by the needles an action comprising any one of or a combination of (1) injecting materials; (2) extracting materials; (3) stimulating organs or tissues; (4) burning or destructing organs or tissues; (d) retracting the needles; and (e) detaching the device.

According to some embodiments of the invention, the method further comprising the step of imaging the area underneath the skin.

According to some embodiments of the invention, conditioned upon the imaging step, the one or more needles are targeted to any one of (1) a blood vessel; (2) nerve organ or fiber; (3) hair papilla; (4) sweat glade; and (5) lesion, identified in the image.

According to some embodiments of the invention, conditioned upon the imaging step, the one or more needles are targeted to any one of (1) dermis tissue; (2) epidermis tissue; (3) subcutaneous fat tissue; (4) muscle tissue; (5) boundaries between these tissues; and (6) intercellular fluid, that are identified by an image created in the imaging step.

According to some embodiments of the invention, the needles are injecting ink to print a tattoo or extract ink from the skin to remove a tattoo.

According to some embodiments of the invention, the step of imaging the area underneath the skin further comprising operating said needles in a division scheme where portion of the needles are transmitting ultrasound signals and another portion of the needles are receiving ultrasound signals.

According to some embodiments of the invention, the step of imaging the area underneath the skin further comprising successive image data capturing steps wherein each said image data capturing step needle tip locations are different.

According to some embodiments of the invention, the step of imaging the area underneath the skin further comprising one or more image data capturing steps, wherein the image data is transferred from the device to a remote computing service and the processed image or the treatment instructions are transmitted back to the device.

According to some embodiments of the invention, the retracting step is performed slowly to prevent an infection from penetrating through the needle penetration tunnel.

According to some embodiments of the invention, the penetrating step in the outer side of the epidermis is performed slowly to prevent pain sensation.

According to some embodiments of the invention, the penetrating step in the outer side of the epidermis is performed fast to prevent pain sensation.

According to some embodiments of the invention, the penetrating step is performed with injecting micro dose of local anesthesia materials.

According to some embodiments of the invention, the penetrating step is performed by plurality of needle penetrating in different time.

According to some embodiments of the invention, the performing step comprises targeting one or more needle to specific location.

According to some embodiments of the invention, the targeting is done to a blood vessel.

According to some embodiments of the invention, the targeting is done to a plurality of blood vessels using a plurality of needles.

According to some embodiments of the invention, the targeting is done to a blood vessels carrying the blood to a specific destination.

According to some embodiments of the invention, the performing step penetrate a plurality of needle that color, burn or destroy the complete volume of a lesion under the treated skin.

According to an aspect of some embodiments of the present invention there is provided a needle system for penetrating to or passing thought an object or an organ comprising: (a) a semiconductor die; (b) one or more needles, wherein the needles slide over the plane of the die; (c) one or more actuators that move the needles relative to the die plane; and (d) one or more actuator drivers controlled by a controller; wherein the controller instructs the needle to penetrate into or to pass through and/or retract from said object or organ.

According to some embodiments of the invention, the one or more said needles are inserted none perpendicularly to anchoring said needle system into said object or organ.

According to some embodiments of the invention, the needle system comprises plurality of semiconductor dies.

According to some embodiments of the invention, a first semiconductor dies is assembled perpendicular to a second semiconductor dies and the second semiconductor dies comprises vias which said needles are passing through those vias.

According to some embodiments of the invention, the needle movement mechanism comprises a ratchet mechanism to restrict the direction of movement and lock said needle movement between movements' steps.

According to some embodiments of the invention, the actuators are electromagnetic or electrostatic or piezoelectric actuators.

According to some embodiments of the invention, the needle has mechanical support to hold the needle and to allow sliding only to a desired direction.

According to some embodiments of the invention, the needle system has friction reduction mechanism to reduce said needle friction during sliding over said die.

According to some embodiments of the invention, the needle is hollow.

According to some embodiments of the invention, the needle system is used for drug delivery or blood extraction or blood analysis or glucose measurements or blood measurements or nerve system stimulus treatment or hair removal or skin lesions removal.

According to an aspect of some embodiments of the present invention there is provided a method for penetrating to or passing thought an object or an organ using a needle system comprising the steps of: (a) attaching to said object or organ a needle system comprising one or more needles, wherein the needles system comprising needles that slide over the plane of a die, and one or more actuators move the needle relative to the die plane, and one or more actuator drivers controlling the actuators using a controller; and (b) controlling the actuators to move the needle to penetrate into or to pass through or retract from said object or organ.

According to some embodiments of the invention, the one or more said needles are inserted none perpendicularly to anchoring said needle system into said object or organ.

According to some embodiments of the invention, the needle system comprises plurality of semiconductor dies.

According to some embodiments of the invention, a first semiconductor dies is assembled perpendicular to a second semiconductor dies and the second semiconductor dies comprises vias which said needles are passing through those vias.

According to some embodiments of the invention, the needle movement mechanism comprises a ratchet mechanism to restrict the direction of movement and lock said needle movement between movements' steps.

According to some embodiments of the invention, the actuators are electromagnetic or electrostatic or piezoelectric actuators.

According to some embodiments of the invention, the needle has mechanical support to hold the needle and to allow sliding only to a desired direction.

According to some embodiments of the invention, the needle system has friction reduction mechanism to reduce said needle friction during sliding over said die.

According to some embodiments of the invention, the needle is hollow.

According to some embodiments of the invention, the needle system is used for drug delivery or blood extraction or blood analysis or glucose measurements or blood measurements or nerve system stimulus treatment or hair removal or skin lesions removal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, some hardware for performing selected tasks according to embodiments of the invention, if not explicitly specified, could be implemented as a chip or a circuit. As software, selected tasks according to embodiments of the invention could be implemented as a plurality of software instructions being executed by a computer or controller using any suitable operating system. In an exemplary embodiment of the invention, one or more tasks according to exemplary embodiments of method and/or system as described herein are performed by a processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a top view of the needle system in close, i.e., initial, position;

FIG. 1B is a cross section of the needle system across line AA designated in FIG. 1A;

FIG. 1C is a top view of the needle system in fully open position;

FIG. 8A is a top view of the die;

FIG. 8B is a cross section of the die across line AA designated in FIG. 8A;

FIG. 8C is a isometric view of the die in open position;

FIG. 9A is a top view of the die;

FIG. 9B is a cross section side view across line A-A designated in FIG. 9A;

FIG. 11A is a top view of a foot toe with a nail fungus treated with a needle system in accordance with the present invention;

FIG. 11B is a longitudinal cross section view of the foot toe with a nail fungus treated with a needle system in accordance with the present invention.

DESCRIPTION OF SPECIFIC EMBODIMENTS OF THE INVENTION

Figure 1A:
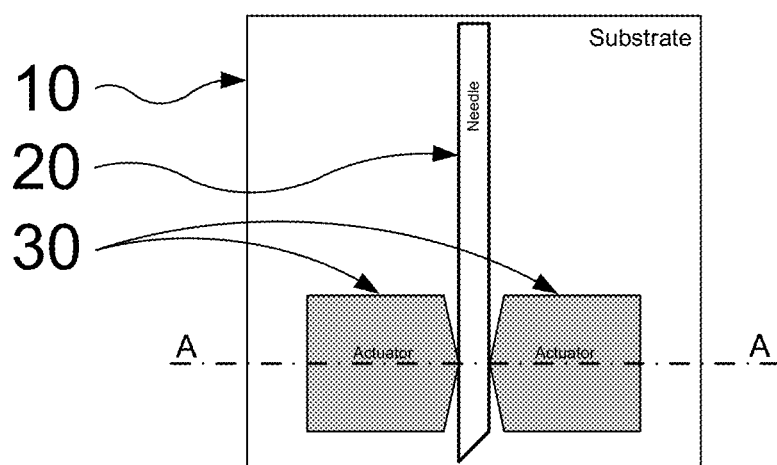
FIG. 1A-FIG. 1C are illustrations of an exemplary embodiment of simplified construction and operation of the present invention needle apparatus.

The present invention, in some embodiments thereof, relates to needles that penetrate objects or organs, and more particularly, but not exclusively, to needles that are used for medical treatments for humans.

The current technology of needle systems does not couple between the needle fabrication and the needle mechanical subsystem that is responsible for the insertion and retraction of the needles to the target object or organ. Currently there are two prominent ways of controlling penetration and retraction of the needle: manually or spring activated. In manual activation, the doctor, nurse or the patient itself sticks and to retracts the needle with his hand. Such an operation has it limitations both in accuracy and in the speed of operation. Spring operated activation uses the mechanical energy stored in a string to inject or retract the needle. This operation is faster but poses excessive strength requirements from the needle. In many cases, the logic behind high speed insertion is to reduce the pain associated with needle insertion and it is based on the fact that if the insertion is fast enough, the nerve system will not be as fast to respond. This is true only if the needle does not strike directly a big enough nerve sensor, e.g., pacinian corpuscle. Spring activation can not control the depth of penetration and only a full penetration design by the spring system activation can be achieved. Usually spring activation needle system is responsible only for the insertion or the retraction and the complement operation is done manually.

The current invention is teaching integrating fabrication of a needle with the fabrication of a mechanical subsystem, which is responsible for the insertion and the retraction of the needle into and from the target object. The needle and the actuator are integrated into a single die or multi die structure using semiconductor fabrication techniques. Both the needle and the mechanical subsystem are fabricated using semiconductor fabrication techniques allowing achieving, among other things, very thin needles. Needles much thinner then stainless-steel needles can be achieved. Another advantage is the ability to manufacture, with a low cost, array of needles that in many applications has an advantage over a single needle system. The medical applications that are being able to be performed using such arrangement are being described hereinafter. Having semiconductor micro mechanical (MEMS) system capability enables very flexible and accurate mechanical operation. For example, the needle may penetrate the object using very small movement steps, with a step resolution of several micro-meters. The penetration speed and force can be preciously controlled over time using digital micro controller that is optionally integrated into the needle system, optionally, on the same die. The ability of very slow insertion of the needle enables novel, not currently in use, scheme to avoid pain during treatment. When a needle is inserted very slowly, the pressure that the nerve system feels is less than the pain threshold hence the patient does not feel the needle insertion. In addition, such scheme, that is not possible in current needle system technologies, enables reduction in the requirement for strength of the needle and enable thinner and more reliable needle system. Furthermore, the ability to stop the penetration in any depth, potentially with the aid of other monitoring signals in the loop, open the doors for many new feature such as (1) penetration to the exact depth in a tissue, e.g., the epidermis, the dermis, or the hypodermis; (2) avoid sticking a blood vassal; (3) targeting to a blood vassal; (4) avoid or targeting nerve sensors; (4) avoid or targeting hair papillae; (5) avoid or targeting sweat glades; and avoid or targeting lesions warts and moles.

As used herein, the term "die" means a rectangle chip fractured from a semiconductor wafer and manufactured in semiconductor foundry by semiconductor fabrication processes. The term "chip" and the term "die" are alternately used in this application and essentially mean the same. Note that the die is not necessarily made of semiconductor material rather is manufactured using facilities that are usually used to fabricated semiconductors dies.

As used herein, the term "substrate" means the material layer the wafer is made of which all additional layers and structure are fabricated on top of it.

Optionally, the needle system comprises an array of needles enable activation of some of the needles in this array selectively based on the needle location.

Before explaining at least one embodiment of the invention in detail, it is to be understood that the invention is not necessarily limited in its application to the details of construction, fabrication techniques and the arrangement of the components and/or methods set forth in the following description and/or illustrated in the drawings and/or the Examples. The invention is capable of other embodiments or of being practiced or carried out in various ways.

Figure 1B:
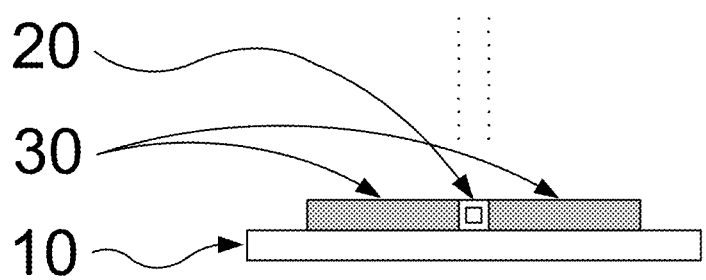
Figure 1C:
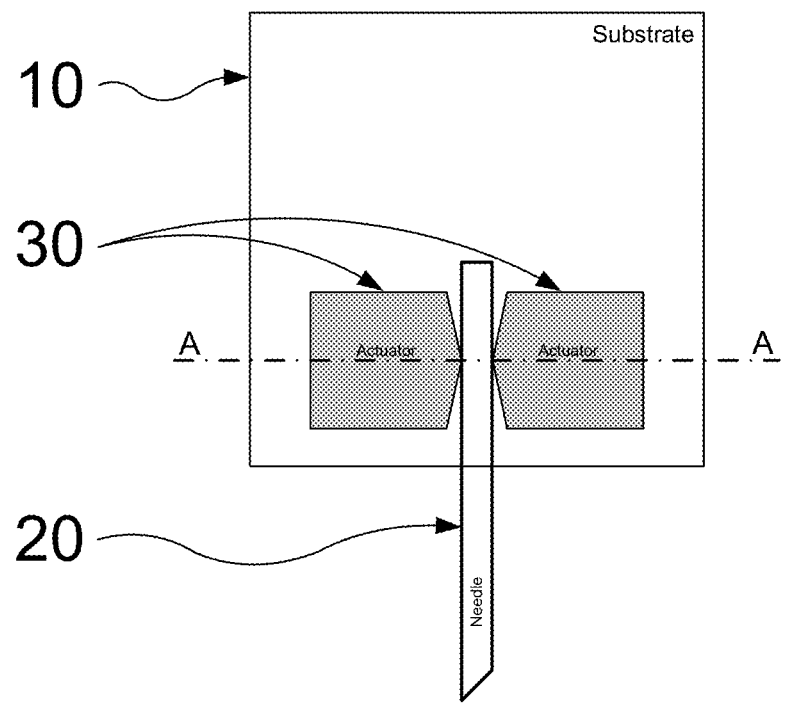

For purposes of better understanding some embodiments of the present invention, as illustrated in FIGS. 1-12 of the drawings, reference is first made to FIG. 1. FIGS. 1A-1C illustrate a principle simplified construction and operation of the present invention. FIG. 1A presents a top view of the needle apparatus in close, i.e., initial fabricated position. FIG. 1B presents a cross section view of the needle apparatus across line AA designated in FIG. 1A. FIG. 1C presents the top view of the needle apparatus in fully open position. The simplified needle apparatus comprises a die substrate 10, a needle 20 and an actuator 30. Needle 20 may be fabricated as a floating element over substrate 10 so it can be moved or slid over substrate 10. Needle 20 is attached to actuator 30 that moves or slides the needle relative to the die substrate 10. In specific, needle 20 can exceed die substrate 10 edges and get out of the die boundary in order to penetrate or pierce a target object if the object is attached or come in to proximity with the die edge. Needle 20 may be fabricated using silicon, silicon oxide, or any other materials that can be grown or printed on die substrate 10 using semiconductor fabrication processes. To achieve a floating needle structure the needle may be fabricated on top of a thin temporary layer (for example silicon oxide) that is etched away after needle fabrication. To reduce the friction between die substrate 10 and needle 30, a small dimples array optionally imprinted. The needle 30 and actuators 20 are build such that a full accurate control of needle insertion is possible.

Needle 30 may be configured to move in plane with the die substrate 10 plane or out of the die substrate plane 10 as demonstrated in FIGS. 8 and 9.

Both the length of insertion and the velocity of insertion may be adjustable. It is also possible to retract the needle back to its initial position inside die substrate 10. Retraction time and retraction velocity may also be fully controlled.

A single die may comprises a plurality of actuators and a plurality of needles with any one of or a combination of one to one, one to many and many to one actuators to needles relationships.

As used herein, the term "actuator" means an element or a component or a circuit or a complex of elements that configured to mechanically move or displaced another element, e.g., a needle.

As used herein, the term "needle" means an elongated element that is configured to mechanically pierce or penetrate an object. The tip of the needle may be sharp to ease the penetration to the object. The strength, length and width of the needle may varies depend on the pierced object and the purpose of the use. The needle may be hallow in order to inject or sucks materials through the needle. Needle may have additional elements such as conductive or resistive elements over the elongated body or in the tip area.

Figure 2:
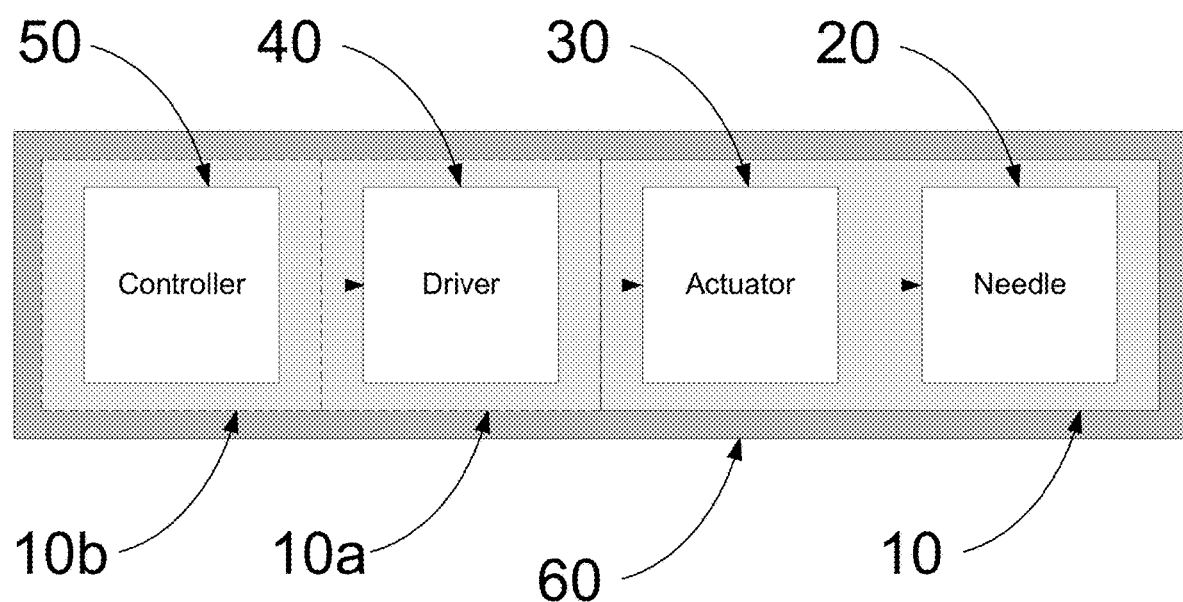
FIG. 2 is a block diagram of a minimal simplified needle system in accordance with the present invention.

Reference is now made to FIG. 2. FIG. 2 illustrates a block diagram of a minimal simplified needle system in accordance with the present invention. Needle 20 is a needle as illustrated in FIG. 1. Actuator 30 is in contact with Needle 20 and can move needle 20 between initial position and fully open position, as illustrated in FIG. 1. Actuator 30 moves needle 20 according to signal from an actuator driver 40. Actuator driver 40 drives current or voltage signals to activate actuator 30. Optionally, driver 40 drives multiple signals to activate actuator 30. Optionally, driver 40 drives complex signaling like sine waves, pulse waves or any complex time function signals to activate actuator 30. Optionally, driver 40 drives digital signaling to activate actuator 30. Typically, driver 40 is implemented using analog electronic elements such as transistors. As used herein, the term "actuator driver" means an element or a component or a circuit or a complex of elements that configured to electrically signaling and controlling the actuator operation.

Needle system comprising a controller and one or more dies as illustrated in FIG. 1. The needle system is controlled by the controller 50. Controller 50 instructs the driver to generate the appropriate signals to move needle 20. Controller 50 determines system level operation parameters, such as, when the insertion of the needle will starts?, for how long in time and in what velocity needle will penetrate?, what will be the depth of penetration?, for how long the needle will be inside the object?, how long it will take to retract the needle?, etc. Typically controller 50 is implemented as a digital micro controller with a processor, memories and peripherals and it is running embedded software on it.

Needle 20 and actuator 30 are fabricated on a single semiconductor die 10 as illustrated in FIG. 1. Driver 40 is optionally fabricated on the same die, i.e., die 10, or alternatively on independent die, die 10a. Controller 50 is optionally fabricated on the same die, i.e., die 10, or alternatively on independent die, die 10b. When needle 20, actuator 30, driver 40 and controller 50 are integrated on the same die, a complete needle system in a single die is implemented. Optionally, die 10a and die 10b are implemented as a single die and the full needle system is implemented as a two die solution. Such a configuration has several advantages and is specifically illustrated and described, later on, in FIG. 7. Optionally, needle system has external package 60. External package 60 size and shape depends on the actual application of the needle system and the object or organ it is aimed to penetrate to. For example, an adhesive patch package may be used to attach the needle system to a skin portion. In a different application the package may contains straps to tight the needle system to the organ. To fulfill sterilization requirements external package 60 may be sealed with a dedicated pierceable membrane to enable needles to get out from package 60.

Figure 3:
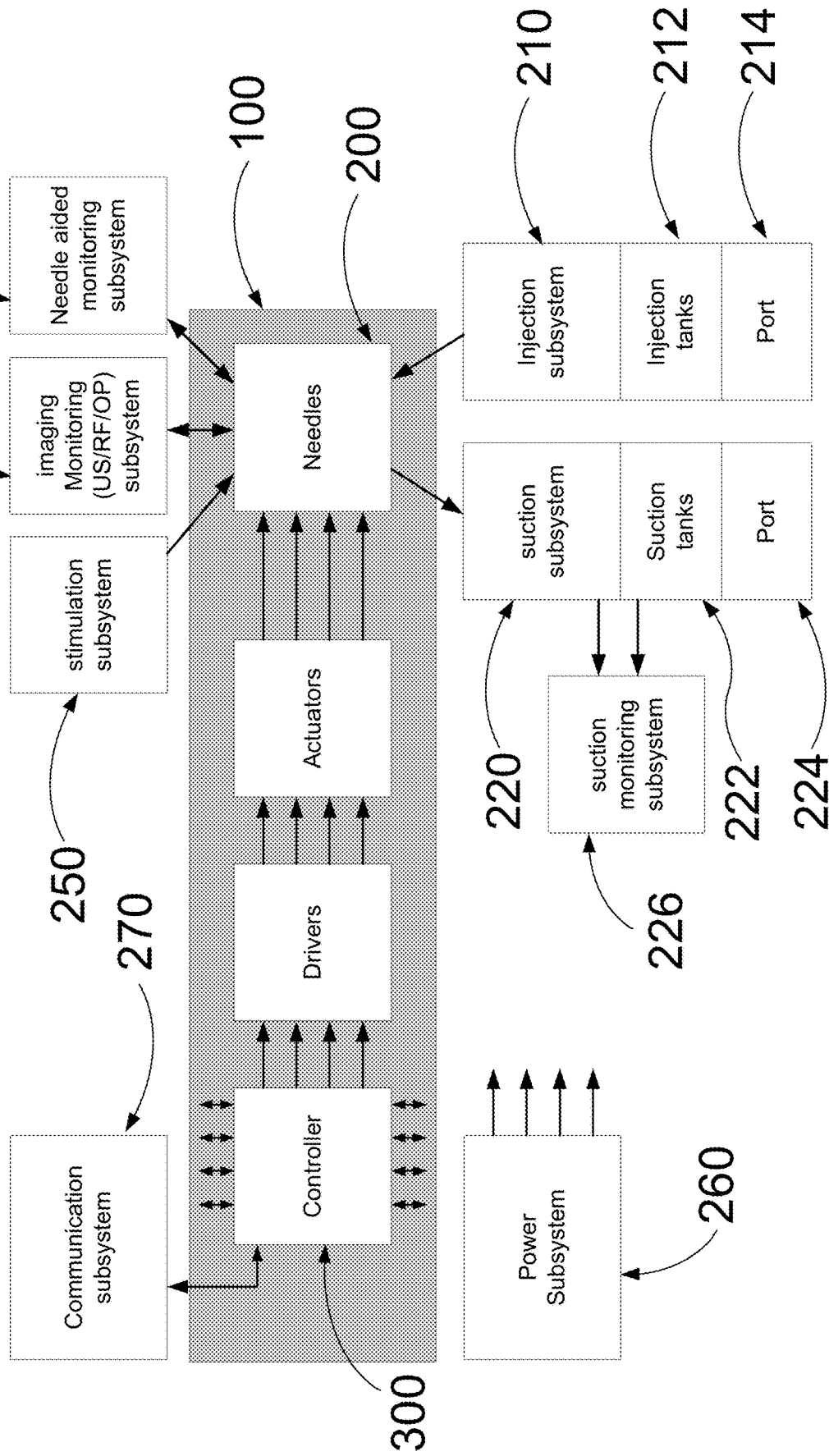
FIG. 3 is a block diagram of a more complete needle system that implement more advanced applications in accordance with the present invention.

Reference is now made to FIG. 3. FIG. 3 illustrates a conceptual block diagram of a more complete needle system that comprising additional blocks to implement variety of applications in accordance with the present invention. The core of the system is needle subsystem 100 that is comprising from one or more needles 200 moved by one or more actuators, driven by one or more actuators drivers and controlled by one or more controllers 300. The plurality of actuators and the plurality of needles may be associated to each other by any one of or a combination of one to one, one to many and many to one relationships. Similarly, the plurality of actuator drivers and the plurality of actuators may be associated to each other by any one of or a combination of one to one, one to many and many to one relationships. Optionally, Needles 200 is attached and in fluid connection with injection subsystem 210 that is configured to inject fluid materials though the needle to the target organ or object. The injection materials are stored in one or more injection tanks 212. Injection tanks 212 are optionally externally refilled using injection port 214. Injection subsystem 210 may be implemented in a the same die using thermal injection, i.e., heating the fluid to rise its pressure, or piezoelectric injection, i.e., press the liquid into the cavity by piezoelectric crystal movement.

Needles 200 optionally attached to a suction subsystem 220. Suction subsystem 220 is in fluid connection with needles 200 and is designed to suck or extract fluid materials from the target organ or object. The extracted materials are stored in one or more suction tanks 222. The material in suction tanks 222 are optionally transferred externally using injection port 224. Optionally, suction materials are transferred to a build in monitoring system 226. Optionally, suction monitoring system 226 monitor the suctioned materials stored in suction tanks 222. Monitoring may be a concentration of a specific molecule in the extracted fluid, e.g., glucose concentration in blood, existence of specific biologic organism such as a specific virus or any other molecule concentration, organism existence or other property of the sampled suctioned material. Suction subsystem 220 may be implemented on the same die using a well-known peristaltic pump structure.

Optionally, needles 200 attached to a needle aided monitoring subsystem 230. Needle aided monitoring subsystem 230 is designed to measure parameters of the needle current state or needle tip surroundings or the target organ/object using needles 200. Since typically needles 200 are electrically conductive, driving electric signal to the needle may revile some desirable properties of the area of the object the tip is located in. For example, measuring the electric resistivity between two adjacent needles that are inserted together can revile the type of tissue the needles are in. Measuring the resistive force the needle is facing during the insertion stage can also help in reviling the tissue the needle tip is reaching. More sophisticated measurements involving injection and detection of ultrasonic waves (US), radio frequencies (RF) waves or optical signals (OP) or any other type of energy injection through the needles is optionally provided. The aim of the energy transmission and energy reflection in needle aided monitoring subsystem is to measure parameters relevant to the actual needle tip in its specific position surroundings.

Optionally, needles 200 attached to an imaging monitoring subsystem 240. Imaging monitoring subsystem 240 is designed to provide the controller a 2D or 3D image of the target organ/object. The image can be constructed using transmission and reception of ultrasonic (US), radio frequencies (RF) or optical signals or any other type of energy transmission and reception that can provide the necessary information. In case needles 200 are constructed as an array, they are also well fitted to be used as the source, the energy guides and the energy sensors for the image monitoring. Optionally, imaging monitoring subsystem 240 is using none attached to needle elements such as transmitters and detectors build-in in the system to create an image independently from needles 200. Imaging monitoring subsystem 240 is connected to controller 300. The image information is used by controller 300 to select the right needle to perform the task optimally and to set the correct or optimal depth for penetration for each active needle. The image information may be also dynamically processed to analyze the actual results of the treatment and to decide its dynamics and its completion. Optionally, the 2D or 3D image is built from successive stimuli done with the needle is located in different locations. Optionally, beam-forming technics is used to focus energy transition or to directional energy reception through array of needles 200.

Optionally, needles 200 attached to a stimulation subsystem 250. Stimulation subsystem 240 is designed to transfer energy through the needle to specific target areas in the target organ/object. Stimuli is ultrasonic (US), radio frequencies (RF), optical signals or any other type of energy that can effect the target organ. Optionally, stimuli are provided to destroy an organ in the treated object. For example, stimuli may be electric signal to create or prevent pains in the nerve system. Stimuli can also be a signal that destroy a nerve sensor or a hair papilla or a sweat glade.

The needle system contains power subsystem 260 that provide energy for operation of all other subsystems. Optionally, power subsystem 260 contains battery. Optionally, power subsystem 260 contains rechargeable battery. Optionally, power subsystem 260 contains charger. Optionally, power subsystem 260 contains wireless charger. Optionally, power subsystem 260 contains power port for external power source. Optionally, power subsystem 260 contains energy convertor that harvest energy from the environment to power the system or charge power subsystem 260 batteries.

The needle system contains communication subsystem 270 that enables communication with other adjacent systems. Preferable communication media is wireless but optionally wired communication is used. Communication subsystem 270 is connected to controller 300. Communication subsystem 270 is optionally connected to the patient smart phone. Controller 300 may get instructions from outside or provide data to the patient and/or the patient health information system, optionally contained processing and storage elements in the cloud. Communication subsystem 270 optionally contains indicators, displays, buttons and/or keyboards to locally interact with the patient or, in general, the needle system operator.

The Needle Movement System

The following section with its accompanying figures is describing in greater details the design, fabrication and mechanical aspects of the needle actuation and needle movement. There are four elements in this discussion that affect each other: (1) the step motor or step actuation and step movement of the needle; (2) the locking mechanism or ratchet mechanism that restrict the direction of movement and locks the needle between movement steps which is optionally needed to combat resistive forces from the target object to the needle movement that try to force the needle back to its previous position; (3) the sliding support elements that direct and enable the movement of the needle only in the desired directions, and hold the needle against shear forces etc; and last, (4) the friction between the needle and the support elements and die or substrate, that in general, resist the movement of the needle.

Figure 4:
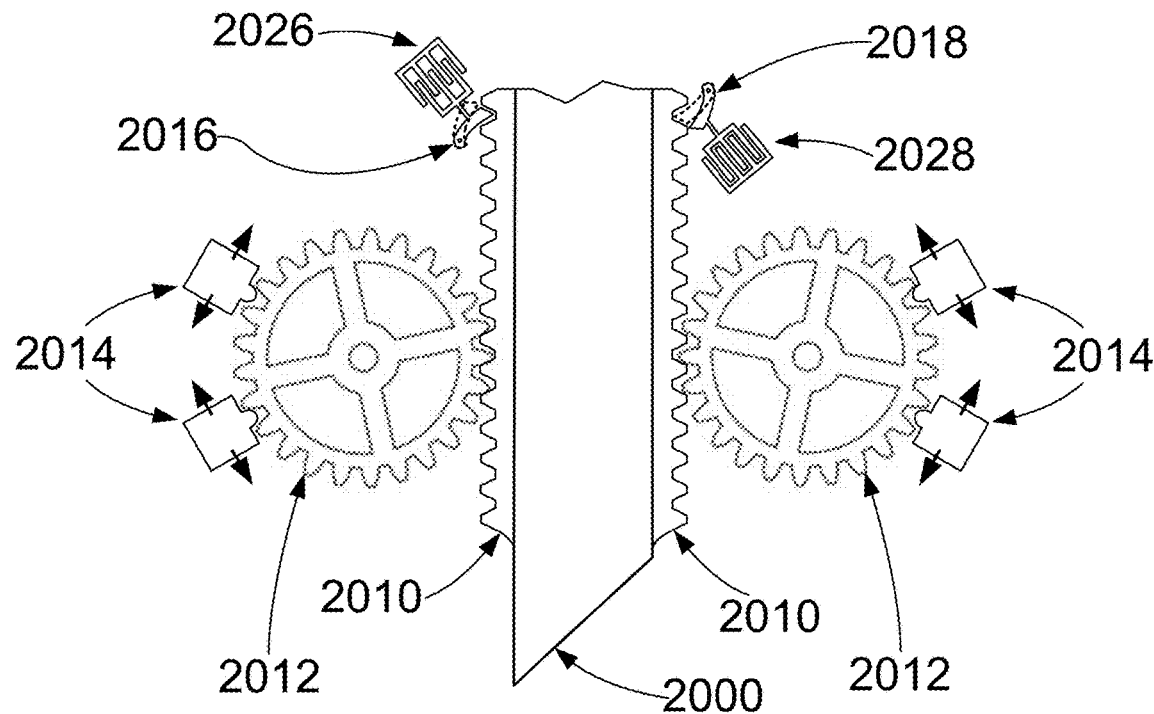
FIG. 4 is a is top view of a needle movement subsystem with force transmission and ratchet mechanism imprinted on the die plane in accordance with a preferred embodiment of the invention.

Reference is made now to FIG. 4. FIG. 4 illustrates an exemplary embodiment of actuation subsystem to implement needle movement with force transmission and ratchet mechanism. The figure is a top view of the structure imprinted on the die plane. Teeth bars 2010 are fabricated in the sides of needle 2000. The linear movement of the needle is generated by the rotation of teeth wheels 2012. Rotating a teeth wheel on MEMS is a well-known in the art and many actuators and MEMS engines architectures have been developed and can be used to convert actuation cycles to teeth wheels 2012 rotation. Variable transmission power techniques may also used to achieve the required delivered force to needle 2000. Alternatively, actuators can directly drive teeth bars 2010 and for example, create a move of one tooth displacement in each actuation step. In the exemplary actuation presented in the figure, a four actuators 2014 are presented. Each two actuators 2014 drive a single teeth wheel 2012. Note that teeth wheels 2012 are used as power transitions that both collect and sum the power from actuators 2014 and convert the direction of power from diagonal to parallel to the needle axis. To provide multi-activation cycle of the actuator without teeth wheel 2012 rotating back, a staggered activation of each actuator 2014 pair attached to the same teeth wheels 2012 is used. In this case, careful design of the teeth geometry allow actuator 2014 to perform its backward movement while the other actuators 2014 perform it forward movement and vise versa. In this way, the forward movement will rotate the wheel while the backward movement will not rotate the wheel. Alternatively, actuator 2014 movement cycle is slightly elliptical allowing movement in one direction to rotate teeth wheel 2012 and to disconnect from the teeth wheel 2012 hence not rotate the wheel in the other direction. In addition to the needle movement subsystem, a ratchet mechanism based on the existence of teeth bars 2010 is presented in the figure. The ratchet mechanism may be one way ratchet that ensures no backwards movement during penetration or ensure no forward movement during withdrawal of the needle. Optionally or alternatively, two-way ratchet can be used as illustrated in FIG. 4.

A ratchet tooth 2016 prevents penetration movement and a ratchet tooth 2018 prevents withdrawal movement. Both ratchet teeth 2016 and 2018 can be active or inactive. In the figure, ratchet tooth 2016 is active and ratchet tooth 2018 is inactive so the needle in this case can not penetrate but can retract. Actuators 2026 control ratchet tooth 2016 and actuators 2028 control ratchet tooth 2018. Actuators 2026 and 2028 push the teeth to activate the ratchet operation and pull the ratchet teeth to deactivate the ratchet operation.

Figure 5:
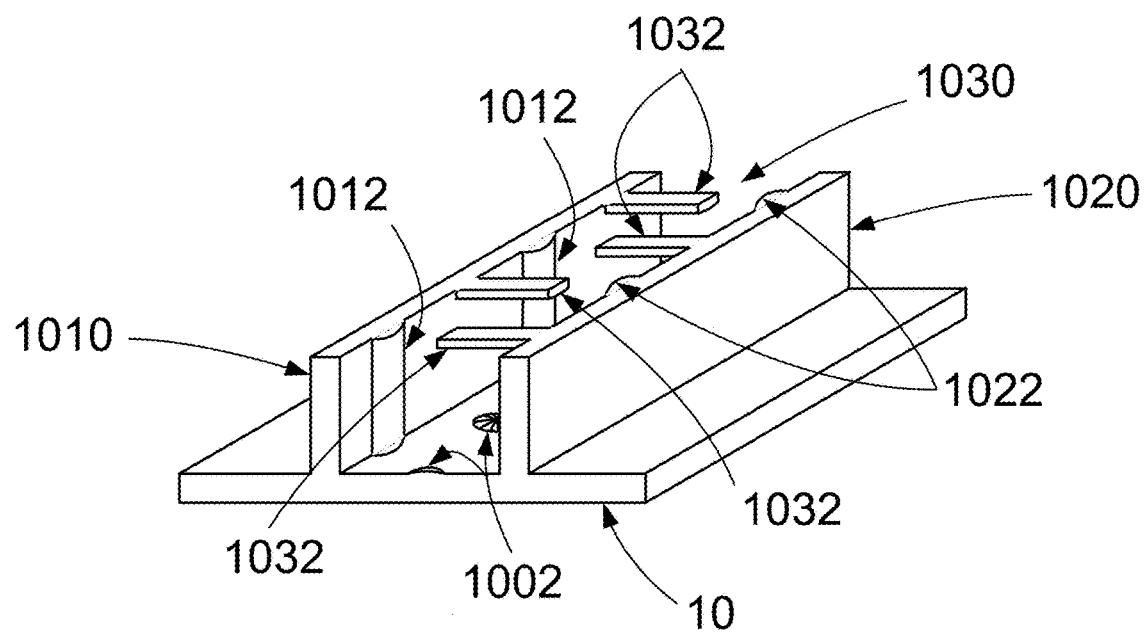
FIG. 5 is an isometric view of needle sliding support and friction reduction subsystem imprinted on the die plane in accordance with a preferred embodiment of the invention, for clarity the needle itself is not shown and only the geometric concepts, not in scale, are shown.

Reference is made now to FIG. 5. FIG. 5 illustrate an exemplary embodiment of needle sliding support and friction reduction subsystem. The figure is isometric view of the imprinted structure but for clarity the needle itself that is imprinted together with sliding support and friction reduction subsystem is not shown. For clarity, the figure is not in scale and only the geometric concepts are shown. The bottom part of the sliding support is the die 10. Die 10 is optionally coated with other layers. To support the sliding, left wall 1010 and right wall 1020 are fabricated. The needle itself is fabricated inside the needle cavity 1030. To reduce the friction of the needle with needle cavity 1030 boundaries, the surface of cavity 1030 is spotted with smooth rounded bumps. The floor of needle cavity 1030 is covered with rounded bumps 1002. Left wall 1010 is covered with bumps 1012. Fabrication constrains limit bumps 1012 to be rounded only in the axis parallel to die 10 plane rather than be rounded in both dimensions. Optionally, two dimensions rounded bump are used. Similarly, right wall 1020 is covered with bumps 1022. To support the needle from the top sides, rods 1032 are fabricate. Rods 1032 surfaces that face needle cavity 1030 are rounded as well to reduce friction. Alternatively, the top support of needle cavity 1030 is fabricated by another die that assemble as the cover package of the needle system. In an exemplary embodiment of the invention, the needle has mechanical support to hold the needle and to allow sliding only to a desired direction.

Friction and wear are well known issue in MEMS moving parts and there are many ways known in the art to reduce friction in MEMS devices. Before naming a few it is to be understood that since the needle in most applications, as described hereinafter, is inserting and retracting the object only once and in slow motion, the friction and wear is less of a problem in the present invention in comparison to other MEMS device where the elements are more frequently or constantly moving. Having said that, the other known methods to reduce friction includes smoothing the sliding to surfaces with different type of etching, coating the surfaces with different type of materials, lubricating the sliding surfaces with liquids or gases. Using micro balls bearing is another option. Another class of methods is to keep the sliding surface apart using electrostatic or electromagnetic forces. In this case, the friction may be used as a ratchet mechanism and the needle is forced to detach from the sliding support only when the step actuation is active, i.e., only when the needle moves.

Many types of MEMS actuators can be used to move or drive the needle. The most common ones are electro-static, electro-magnetic, thermal and piezoelectric. Piezoelectric electric actuation is being a good choice since there are well known ways to implement a step motor with locking (ratchet) mechanism and ultrasonic vibration of the needles is also possible as illustrated in FIG. 6.

Figure 6:
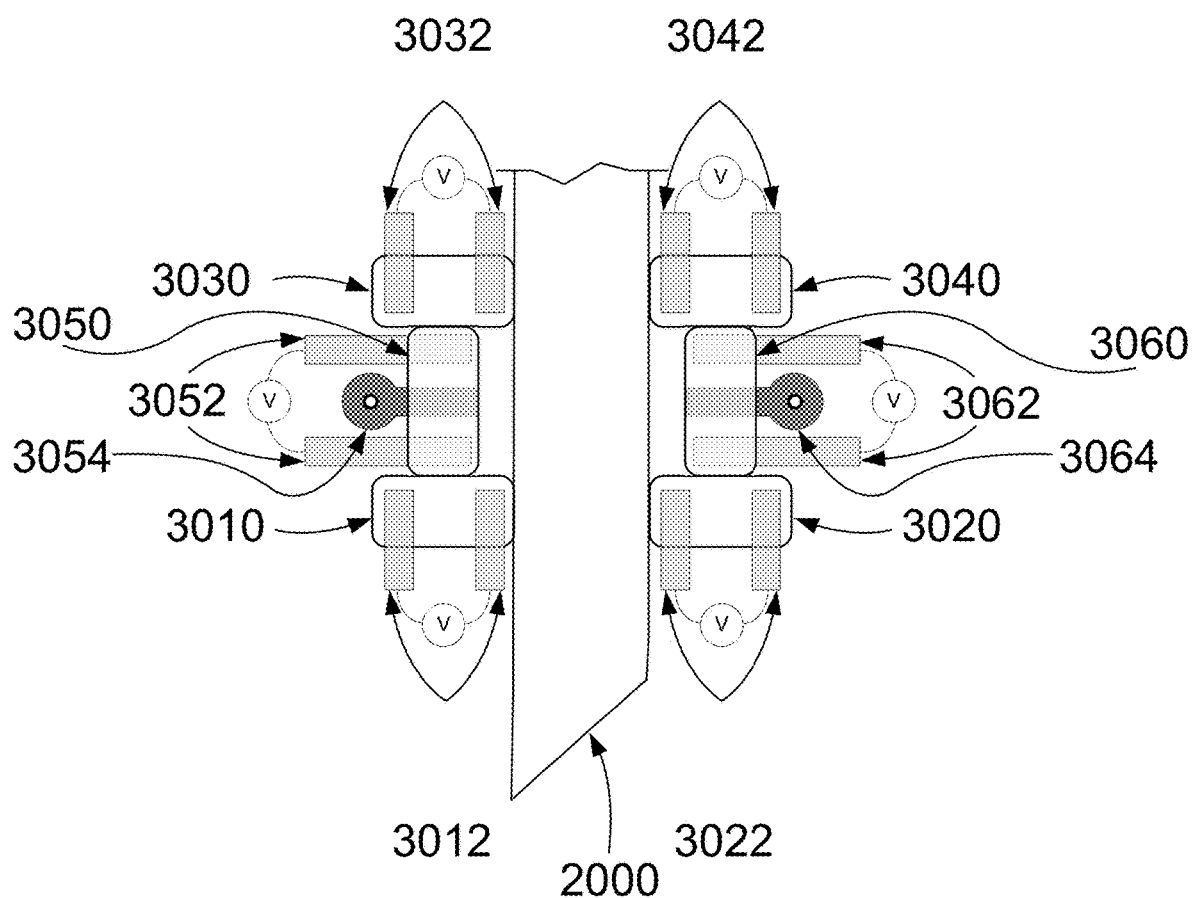
FIG. 6 is a top view of needle actuation and ratchet subsystem using piezoelectric actuators imprinted on the die plane in accordance with a preferred embodiment of the invention, for clarity only the relevant elements are shown.

Reference now made to FIG. 6. FIG. 6 illustrates an example of needle actuation and ratchet subsystem using piezoelectric actuators. The figure is a top view of the imprinted structure and for clarity only the relevant elements are shown. In rest position, needle 2000 is locked by four piezoelectric crystals 3010, 3020, 3030 and 3040. Each piezoelectric crystal 3010, 3020, 3030 and 3040 have a pair of electrodes 3012, 3022, 3032 and 3042 located on the crystals edges. Applying positive voltage, i.e., voltage in the same polarity as the piezoelectric crystal, to electrodes 3012, 3022, 3032 and 3042 expend the crystals, hence increase the gripping force on needle 2000 and increase the locking of the needle to its position. Applying negative voltage to electrodes 3012, 3022, 3032 and 3042 contract the crystals, hence free the needle to move. The full step motor structure contains additional two piezoelectric crystals 3050, 3060 each one of them is located in opposite side with respect to needle 2000. Electrodes 3052 are connected to piezoelectric crystal 3050 and electrodes 3062 are connected to piezoelectric crystal 3060. Piezoelectric crystal 3050 is mechanically attached to the die using anchor 3054. Piezoelectric crystal 3060 is mechanically attached to the die using anchor 3064. During needle insertion motion, i.e., motion downwards in the figure, the needle system controller initiates a specific sequence of instructions as describe herein. In the first step, crystals 3030 and 3040 expand and crystals 3010 and 3020 contract so that the needle is hold only by crystals 3030 and 3040. Next, crystals 3050 and 3060 contract and since crystals 3050 and 3060 are to anchored to the die needle 2000 move downwards. Next, crystals 3010 and 3020 contract and hold needle 2000. Next, crystals 3030 and 3040 contract therefore they release their grip from needle 2000. The next step is expanding of crystals 3050 and 3060 that cause needle 2000 to further move downwards. This cycle can continue as long as the controller wants to insert needle 2000 further into the target organ or object. To retract needle 2000 a similar sequence is applied but now the controller contracts crystals 3050 and 3060 when crystals 3010 and 3020 hold needle 2000 and expands crystals 3050 and 3060 when crystals 3030 and 3040 hold needle 2000. Other structures of piezoelectric configuration with different structure of crystals and electrodes may be used as well. This mechanism can also be used as an ultrasound transducers, i.e., ultrasound transmitter and receiver, to capture an image of the object using the needles. In order for the needle to acts as an ultrasonic transmitter, the needle is gripped by crystals 3010 and 3020 or by crystals 3030 and 3040 and crystals 3050 and 3060 electrodes are fed by electrical signals that vibrate the needle in ultrasonic frequencies. Similarly, for the needle to act as an ultrasonic receiver, the needle vibrates by the received ultrasonic wave and crystals 3050 and 3060 are contracted or expanded by the impinging ultrasonic wave and create an electronic signal. The signal created by crystals 3050 and 3060 electrodes 3052 and 3062 are amplified and feed a monitoring subsystem. Conditioned upon the transmitted and received ultrasound signals the monitoring subsystem generate an image of the object the needles are in contact with. Needle vibration can act also as a stimuli and a source of heating.

System Integration and Packaging

Figure 7:
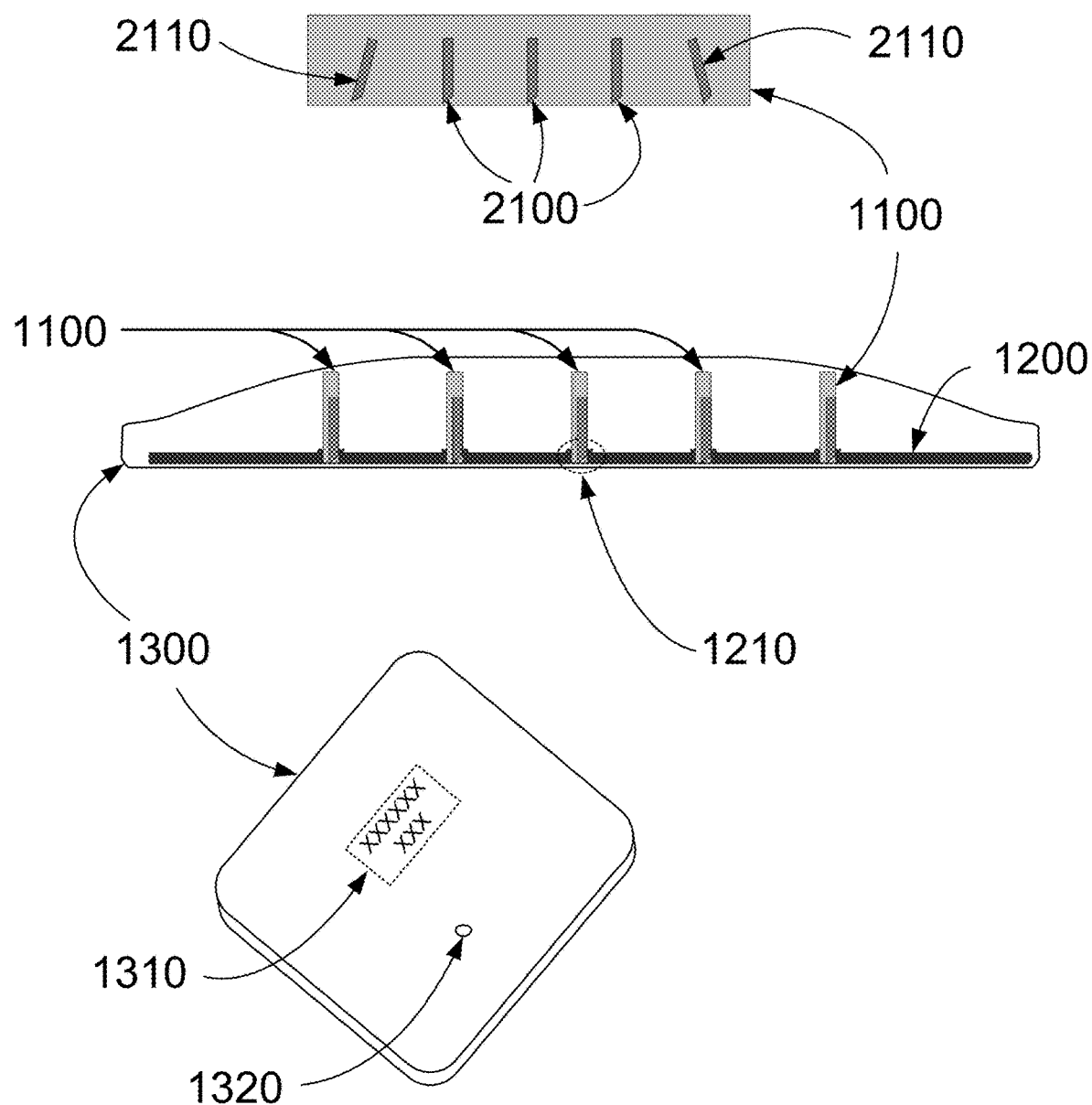
FIG. 7 is a full needle system assembly view in accordance with a preferred embodiment of the invention.

Reference now made to FIG. 7. FIG. 7 illustrates an exemplary embodiment of a complete needle system assembly according to the present invention. FIG. 7 contains three views of the system and its components: in the top of the figure, a side view of MEMS needle chip 1100 in accordance with the present invention is presented; in the middle of the figure, a cross section of adhesive patch package 1300 contains several MEMS needle chips 1100 and one system chip 1200 is presented; and in the bottom view of the figure, an isometric view of adhesive patch package 1300 is presented. In this exemplary embodiment, MEMS needle chip 1100 contains five needles. Optionally, MEMS needle chip 1100 contains 10-100,000 needles. The two needles in the die edges, needles 2210, are tilted outwards. When needles 2210 are inserted into the target organ they provide additional anchoring effect to adhesive patch package 1300. The other three needles 2100 are vertically placed and are inserted perpendicular into the target organ. Adhesive patch package 1300 is a sealed package with adhesive material at its bottom side that glue the package to skin of the target organ. Inside package 1300 there is a system chip 1200 contains standard digital electronic elements comprising the controller and the actuator drivers. The die plane of system chip 1200 is in parallel to adhesive patch package 1300 plane. System chip 1200 contains connection areas 1210 that include vias to enable passage of the needles through system chip 1200, electronic contacts that transfer signals between system chip 1200 and MEMS needle chips 1100 and mechanical support structure to hold the MEMS needle chips 1100 in vertical position. Optionally, adhesive patch package 1300 includes a label 1310 to identify the patch and some UI elements, such as an indicator 1320 that indicates, for example, that the needle system complete its task.

As used herein, the term "via" means a hole passing through the die that enable objects, such as the needle, to pass through it.

Out of Die Plane System Implementation

Figure 8A:
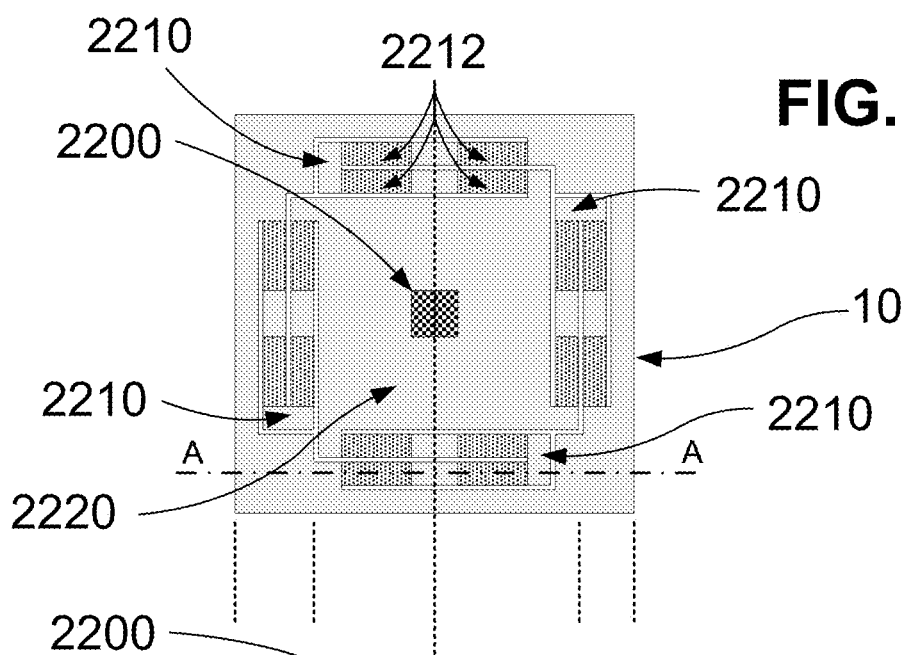
FIG. 8A-FIG. 8C are illustrations of an exemplary embodiment of out of die plane movable needle.
Figure 8B:
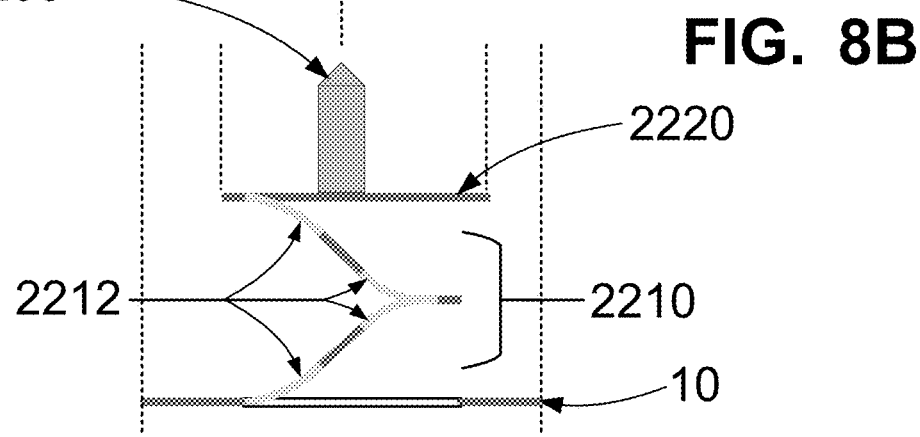
Figure 8C:
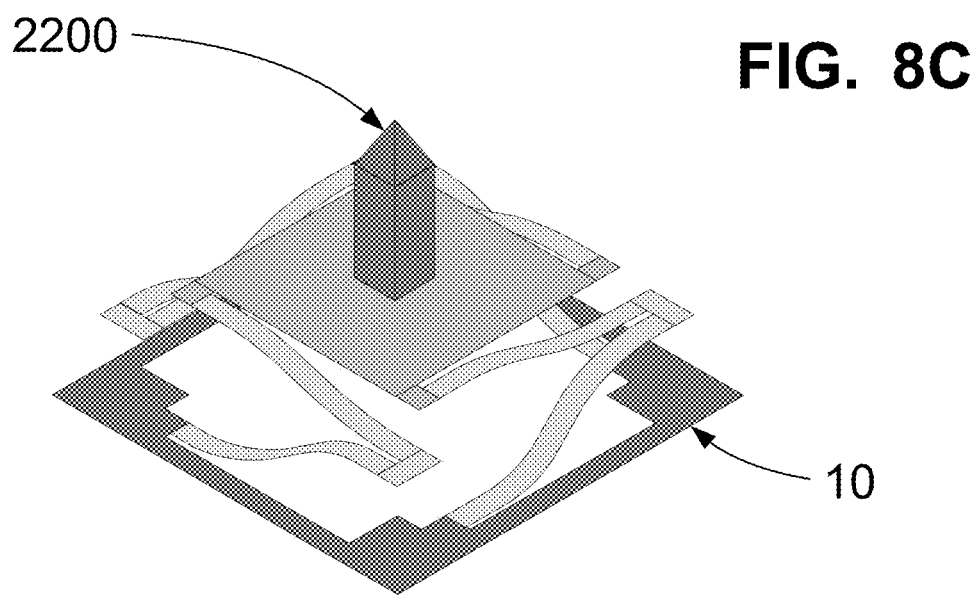

In previous exemplary embodiments, the needle slides on the die plane and the patch that incorporate a 2D array of needle is constructed from a plurality of dies incorporating 1D array of needles. A single die implementation incorporating a 2D array of needles that are move out of plane (e.g., perpendicular to the die plane) are feasible as well as demonstrated in FIGS. 8-9. Reference is made now to FIG. 8. FIG. 8 illustrates an exemplary embodiment of apparatus comprising out of die 10 plane movable needle. Typically, die 10 will have a 2D array with a plurality of such needles. FIG. 8A is a top view of die 10, FIG. 8B is a cross section side view across line A-A of FIG. 8A and FIG. 8C is an isometric view of die 10.

Die 10 comprises a lift-able plain 2220 with a needle 2200 on its center and four folded strips 2210. Folded strips 2210 are located at the four sides of lift-able plain 2220 with one side of each folded strip 2210 connected to lift-able plain 2220 and the other side of each folded strip 2210 connected to the die 10 surface. Each folded strip 2210 is a thermal actuator comprises four resistive segments 2212. When current is driven to the resistive segments 2212 the resistive segments 2212 heat and expand. All resistive segments 2212 are connected in serial so when voltage applied the four folded strip 2210 are bent and lift-able plain 2220 is lifted upwards as illustrated in FIG. 8B and FIG. 8C. The lifting height is a function of the driving voltage or equivalently the driving current. When no voltage (or current) supplied, the lift-able plain 2220 is in the same plane as die 10 (i.e. in zero height).

Figure 9A:
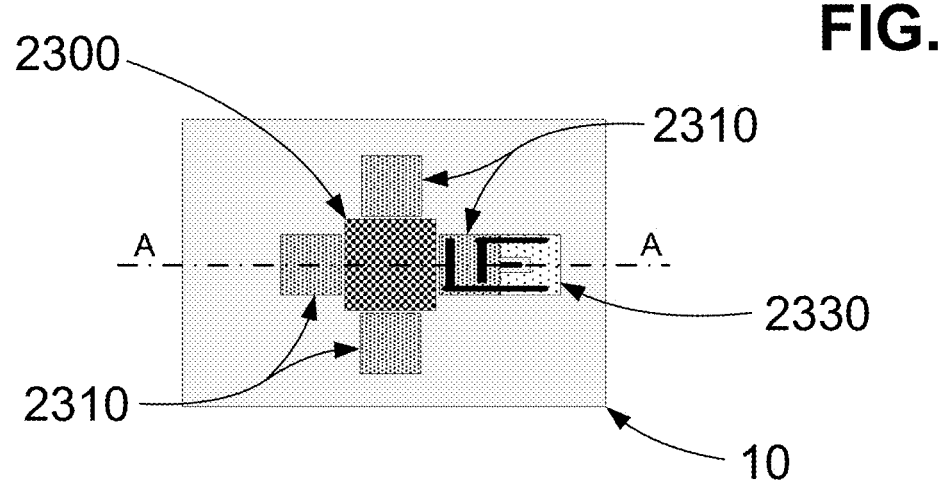
FIG. 9A-FIG. 9B are illustrations of another exemplary embodiment of out of die plane movable needle.
Figure 9B:
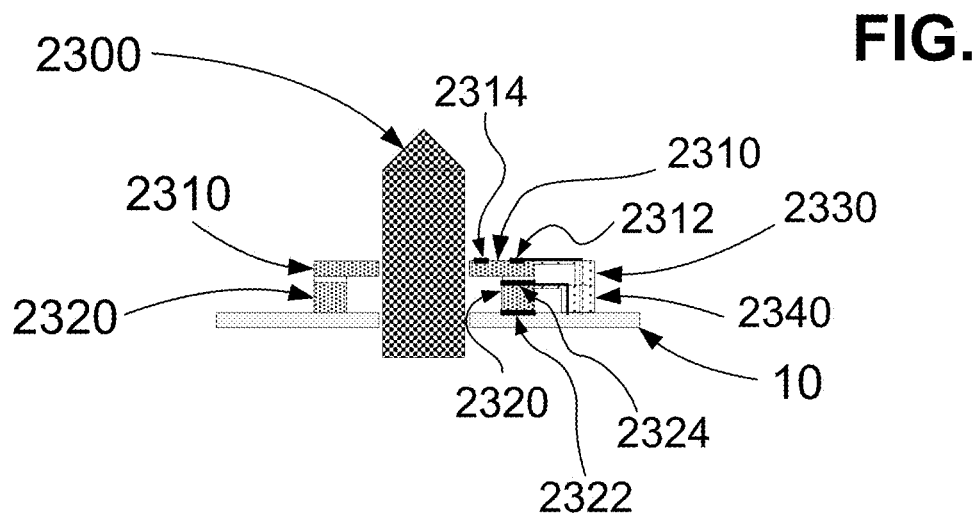

Reference is made now to FIG. 9. FIG. 9 illustrates another exemplary embodiment of single out of die 10 plane movable needle. Typically, die 10 will have an array with plurality of such needles. FIG. 9A is a top view of die 10, and FIG. 9B is a cross section side view across line A-A of FIG. 9A. Needle 2300 is gripped by four piezoelectric crystal 2310 one from each side of needle 2300. The grip of each side of needle 2300 can be held or released by expand or contract each crystal 2310. Each piezoelectric crystal 2310 is laying over another piezoelectric crystal 2320 (seen only from the side view in FIG. 9B) with an electric isolation layer between the two crystal pair 2310, 2320. Four pairs of piezoelectric crystal 2310, 2320 surround needle 2300. When the piezoelectric crystals 2320 extract while crystals 2310 hold needle 2300 the needle is lifting up. When the piezoelectric crystals 2320 contract while crystals 2310 hold needle 2300 the needle is retracting back.

Each piezoelectric crystal 2310 has two electrodes, 2312 and 2314, located on the crystals edges (for sake of clarity only the electrodes of the right side crystal has been illustrated in FIG. 9). Each piezoelectric crystal 2320 has two electrodes, 2322 and 2324, located on the crystals edges (for sake of clarity only the electrodes of the right side crystal has been illustrated in FIG. 9). In order to electrically connect electrodes 2312, 2314, 2322 and 2324 to die 10, cantilevers structure is fabricated over die 10. The cantilever structure comprises bottom cantilever 2340 and top cantilever 2330 laying over bottom cantilever 2340. For the sake of clarity only the right side cantilevers structure has been illustrated in FIG. 9. In reality, a cantilevers structure 2330, 2340 is located beside each crystal pair 2310, 2320. The bottom electrode 2322 is laying on surface of die 10, hence is connected easily to conducting traces on die 10. Electrode 2324 is connected to die 10 through cantilever 2340. The connection is done by conductive via inside cantilever 2340 anchor and conductive trace over cantilever 2340 beam. Cantilever beam 2340 is designed to be flexible enough to support crystal 2320 expand or contract. Electrode 2312 is connected to die 10 through cantilever 2330. The connection is done by conductive via inside the anchors of cantilever 2340 and 2330 and conductive trace over cantilever 2330 beam. Electrode 2314 is connected to die 10 through cantilever 2330 as well. The connection is done by conductive via inside the anchors of cantilever 2340 and 2330 and conductive trace over cantilever 2330 beam. The traces on the beam of cantilever 2330 are imprinted in parallel at both side of the beam, as illustrated by the top view in FIG. 9A. Cantilever beam 2330 is designed to be flexible enough to support the movement of crystal 2310 caused by expansion or the contraction of crystal 2320.

Needle 2300 insertion or retraction motion, i.e., motion upwards or downwards respectively in FIG. 9B, is performed by a specific sequence of crystals expansion and contraction in similar manner to the one describes in companion to FIG. 6 hereinabove. The sequence is done using opposite pairs of crystals 2310, one pair grip the needle and the other pair release the needle to perform a movement that do not affect the needle movement. The pairs are alternating their role between grip and release. During needle lock all four crystal 2310 expand to grip needle 2300 tightly.

It is appreciated that other variation of in-die-plane and out-of-die-plane embodiments of needle movement are possible. Other needle style, actuator types and structures as well as support subsystem such as driving and connecting the various elements are all fell inside the scope of the invention.

Needle System Applications

The applications of the hereinabove described needle system are widespread. The needles may be used in industrial application to pierce or puncture materials, fabrication of fabrics and the like. It may also be used, in general, in labs and in specific in biologic labs to manipulate and monitor biologic entities, e.g., cells, bacteria and the like, for research and development or for industrial manufacturing related to the biologic industry. Additionally, the needle system may be used in medical treatment for humans or animals. Applying the needle system to the human skin for medical or cosmetic dermal or hypodermal treatments produce the following advantages:

1) Controlled and accurate slow to fast penetration;
2) Controlled and accurate slow to fast retraction;
3) Opportunity for smart operation and full system integration.

The term "hypodermal treatment" mean any treatment for medical or cosmetic use, that use needle touching the skin or needle piercing the skin and penetrating to any tissue or body organ that is located up to 10 centimeters under the penetrated skin.

System Integration

Manufacturing a full system on a single die or several tightly coupled dies that are assembled in the fab, allows increased functionality, such as monitoring and control capabilities, with reduced costs that open the door for many new applications. Among other functions, the needles can precisely reach target locations, tissues or organs. The tip of the needle may be located precisely in the boundaries between tissues, like the boundary between the epidermis and the dermis or the boundary between the dermis and the subcutaneous fat tissue or between the subcutaneous fat tissue and the muscles. The needle trajectory may avoid targeting organs in the tissues such as blood vessels, nerve system elements, sweat system elements, hair papillae or other organs. The tip of the needle may also be targeted to organs like blood vessels, nerve system elements, sweat system elements, hair papillae or other organs. Using monitoring capabilities in the needle itself, such as mechanical and electrical resistance measurements or other measurements using sensors like ultrasound, RF or optical sensors, the needle system may provide the required information for accurate targeting of the needles. All those features and more, that are described hereinafter, are feasible due to the capabilities of system integration.

General Hypodermal Treatment Method

Generally the method for hypodermic treatment comprising the following steps:
a) attaching to a skin portion a needle system device comprising one or more dies that comprising movable needles;
b) penetrating the skin by moving the needles into the skin;
c) performing by the needles an action comprising any one of or a combination of (1) injecting materials; (2) extracting materials; (3) stimulating organs or tissues; (4) burning or destructing organs or tissues;
d) retracting the needles; and
e) detaching the device.

The method may have additional steps and the performing steps may have additional action and in specific applications, the steps may be a complex sequence of repeating actions condition upon some measurements and monitoring activities.

Infections Immunity

Due to the slow retraction property, the invention can solve a major problem of hypodermic needle treatments, which is a risk of possible infection. When a needle retracts at once, in the first few minutes there is an open tunnel for bacteria and viruses exist on the skin or in the air to penetrate the body through this tunnel, those infections may be very dangers. With the present invention, when applying slow retraction, the skin tissue is given the time to repair itself and close the opened tunnel as the needle retracts and before the needle leave the skin and expose the tunnel to the pathogens exist on the surface of the skin or in the air. Eventually, when the needle is fully retracted, the tunnel in the skin is already closed and the possibilities for infections to penetrate the skin are illuminated. In an exemplary embodiment of the invention, the retraction is performed slowly to prevent an infection from penetrating through the needle penetration tunnel. The term slowly with respect to this issue is more than 1 minutes per centimeter.

2D/3D Imaging using Ultrasound Technics by Vibrating the Needles

In an exemplary embodiment of the invention, each needle is capable to vibrate and may create sound wave as well as measure vibrations and receipt sound wave. This capability is possible by using a piezoelectric actuation described above. The piezoelectric crystals can vibrate in high frequencies, i.e., can create vibration in frequencies of up to few Giga Hertz. High bandwidth ultrasound signals are transmitted by the needle to gain high imaging resolutions. The ultrasound signals can be a serious of pulses or wideband signals like Direct Sequence Spread Spectrum (DSSS) signals, OFDM signals or any other signal modulation technics to provide accurate measurement of the time of arrival of the echoes of the transmitting ultrasound signals. The echoes are created by the underlying tissues and reveal the tissues structure. To increase the imaging quality, the signal may be cooperatively transmitted using a plurality of needles with a controlled phase between the different needles. Such technics, known also as beam-forming, directs or focuses the ultrasound wave to specific direction. By changing the phases the imaging system can scan different directions underneath the needle system in 1D or 2D scanning ultrasound beam. Similarly, beam-forming may be performed in the reception, focusing the reception of the echo ultrasound waves only to reception from a specific direction.

There is a physical limitation on the ability of the needle to transmit and receive simultaneously. One way to overcome this limitation is to use each needle, in any specific time, either as a transmitter or a receiver. Since the needle system have a plurality of needles, the following technics for performing both transmission and reception are employed: (1) time switch: all needles transmit for a short period then all needles switch to receive mode to receive the echo signals; (2) portion of the needles are always in transmit mode while the other portion is in receive mode; (3) frequency/time/code division schemes: each set of needle get a division scheme to transmit and division scheme, or possibly a plurality of division schemes, for receive. The transmitted signal is suppressed or significantly reduced from the received signal by filtering it out using the division scheme.

To further enhance the image quality, each needle tip location may change during successive image data capturing steps. For example, if in first step all needles are moved to have initial contact with the skin and then a first analysis step is made, then in the next step, some or all of the needles are inserted slightly deeper into the skin (an increment of 1-10 micron may be a typical such increment) and then another image data capturing is performed. The two image data are combined to generate a single improved resolution image. Optionally, more such analysis steps are made with different needle tip locations to achieve the resolution that is needed for the specific treatment.

In an exemplary embodiment of the invention, the ultrasound processing include Doppler shift measurements to identify blood vessels. This is done by the well-known technics that filters the echoes from the flowing blood by the Doppler shift this flow creates. Optionally, the direction and velocity of the blood stream in the vessel is measured as well. The measure of the blood velocity is done by the amount of the Doppler shift presented in the ultrasound echoes.

In an exemplary embodiment of the invention, the ultrasound image is taken once in the beginning of treatment. Optionally, a plurality of images are taken during the treatment.

In an exemplary embodiment of the invention, the received image data are transmitted to a computing services outside the needle system, e.g., a near-by smart phone or a computing server in the cloud, and the processed image or optionally the treatment instructions are transmitted back to the needle system.

Figure 10:
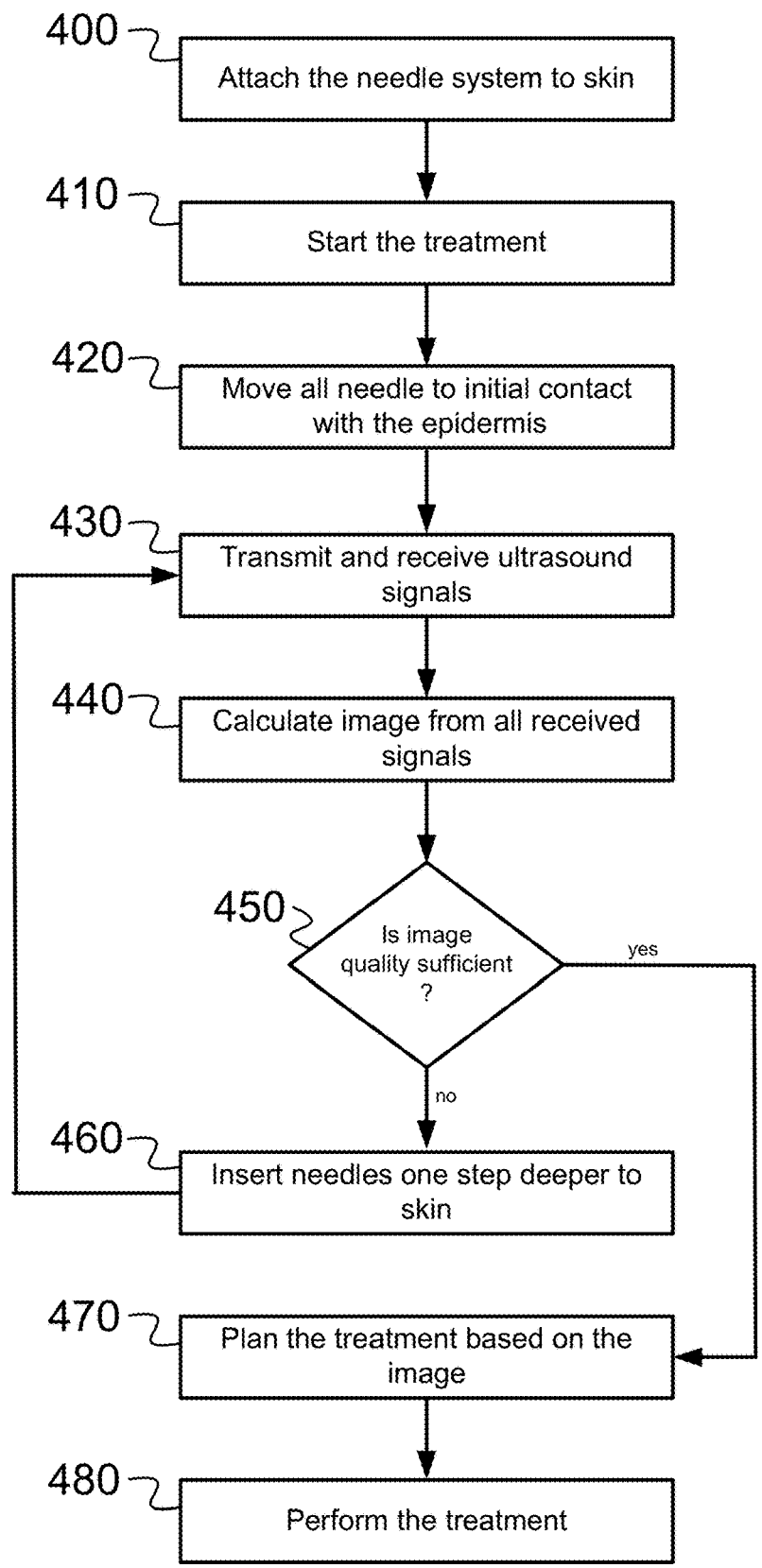
FIG. 10 is an exemplary flow chart of a treatment based on performing imaging using the needle system.

Reference is now made to FIG. 10. FIG. 10 is an exemplary flow chart of a treatment based on performing imaging of the area underneath the skin using the needle system. In the first step 400, the needle system is attached to the skin. Upon completion of the first step, the needle system, either automatically by detecting that the attachment is complete, or manually by instruction from the patient, move to the second step 410 which is the starting step of the treatment. Step 410 performs initializations, if needed, and the system move to step 420 which positions all needles in initial contact with the epidermis. The initial contact may be detected by the mechanical resistive force of the skin, by electrical resistance change or the like. When all needle are in contact with the epidermis, the needle system collect image data in step 430 by transmitting and receiving ultrasound signal through the needles. The specific multiplexing scheme between the transmitting and receiving is one of the schemes discussed hereinabove. When all signals received, in step 440 a 2D or 3D image is calculated. Image quality requirements should be in accordance to the requirements of the treatment. For example, if the treatment is a drug delivery to a blood vessel, a proper blood vessel (e.g., one with enough blood stream capacity) should be clearly detected. If for example, the treatment is hair removal, the hair papillae under the needle system should be clearly detected. In step 450, the needle system determines if the image quality criteria for the treatment is met. If yes, system goes to step 470 and plan the treatment based on the image. For example, if the treatment is drug delivery to a blood vessel, the system plan which needle is used to penetrate the skin and reach the blood vessel as well as the depth of penetration that is needed for this needle to reach the blood vessel. If the treatment is hair removal, the system plan include finding all hair papillae that can be reached and assign for each hair papilla the needle that will reach it, as well as the depth of penetration that is needed for each one of the selected needles. If in step 450, the image quality criteria does not met, the system goes to step 460 in which some needles are inserted bit deeper into the epidermis in order to collect more, from a bit different location, image data to improve the image quality. When needles are in their new position, the system goes to step 430 to retransmit and receive more ultrasound signals and collect more image data. Steps 430-460 can be iterated as long as necessary. Finally, from step 470 the system goes to step 480 and perform the treatment. For example in the drug delivery case, the selected needle reach the target vessel and inject the drug to the vessel with the desired quantities and time duration. In the case of hair removal, the needles reach the hair papillae and destroy the hair papillae. The destruction operation may be done by injecting a toxic material, by applying electric voltage to the papillae through the needles, by vibrating the needle inside the papilla or the like.

In exemplary embodiment of the invention, the imaging of the area underneath the skin comprising successive image data capturing steps wherein in each said image data capturing step locations of the tip of the needles are different.

In exemplary embodiment of the invention, the imaging of the area underneath the skin comprising one or more image data capturing steps, wherein the image data is transferred from the device to a remote computing service and the processed image or the treatment instructions are transmitted back to the device.

Painless Penetration and Retraction

One of the major drawback in medical hypodermic needle treatments is the pain created by the needle stings and the fear associated with it. The needle system presented herein is able to avoid the pain and the fear in the following ways. First, the precise time of the needles penetration is determined by the system and is not known to the patient, hence illuminates the psychological effect of the fear. For illumination of the pain sensation itself, several technics, described hereinafter, and any combination or subcombination of them are used by the needle system. Before presenting these technics, a short introduction on the sources of the stinging pain is presented.

The main source of the stinging pain sensation is a dense net of nerve ends layer reside on the outer side of the epidermis just below the layer of dead skin cells that forms the outer surface of the skin. The nerve end net layer thickness is dozens of micron. Any penetration (i.e., hitting these nerve ends) create a nerve activation potential but in order for a pain sensation to be felt, a plurality of nerve activation potentials need to cross a threshold. The integration of many such activation potential is done both in time and in space. The integration and threshold crossing processing is done by sensory neurons in the spinal cord. These sensory neurons generate a pain signals (another activation potential) transmitted to the brain.

The threshold is not fixed and have complex behavior, it raised by other nerve system sensors in the area such as pressure and heat sensors (this is way rubbing the area during a sting reduce the sting pain sensation). The threshold is reduced to some extant if same sensing is sustained or during fear or other type of mental stress and so on. From the following explanation one can deduce the well known facts that smaller needle (less space integration) and faster stinging (less time integration) reduce the pain sensation.

The pain reduction technics used by the needle system according to the present invention are the follows:

(a) Needle staggering: Instead of having one big needle, system needle may use several smaller needle that are crossing the epidermis one at a time. Such a staggering scheme prevent the nerve activation potentials created by the nerve end net layer to cross the threshold.

(b) Very fast epidermis crossing: with the accurate control over the speed of the needle, the needle system can drive the needle to pass through the thin nerve end net layer faster to reduce the time and avoid crossing the threshold.

(c) Very slow epidermis crossing: another opposite technics is to penetrate the thin nerve end net layer very slowly. If the speed is slow enough the threshold is not crossed as well. This is especially good for thicker needles or mechanically weak needles.

(d) Injecting micro dose local anesthesia by the needle tip just before the needle penetrate the thin nerve end net layer.

(e) Stimulate, with another needle, nerve system pressure and heat sensors to rise the pain threshold.

(f) Avoiding hitting nerves sensors and fibers by selecting the right needles with the aid of image driven treatment planning.

(g) Optimize the treatment by image driven treatment planning to minimize penetration of needles during the treatment.

In an exemplary embodiment of the invention, the penetrating step in the outer side of the epidermis is performed fast to prevent pain sensation. The term fast with respect to this issue is more than 100 millisecond per millimeter.

In an exemplary embodiment of the invention, the penetrating step in the outer side of the epidermis is performed slowly to prevent pain sensation. The term slowly with respect to this issue is more than 1 second per millimeter.

Treatments for Kids

Fear from hypodermic needle treatments is a huge problem with kids that refuse to get a hypodermic needle treatment and create a lot of time consumption and frustration for health personal. In an exemplary embodiment of the invention a special friendly design for kids hand watch is provided. The watch have a needle system integrated to the back side of the watch facing the kid wrist. The watch take the attention of the kid using sounds and images display on the top side of the watch, while the needle system painlessly penetrate the kid's skin taking a blood sample, inject a drug or making any other hypodermic needle medical treatment the kids had to do. Other similar devices configured to treatment in other skin locations other than the wrist may be provided as well.

Drug Delivery

Drug delivery is one of the most exploited hypodermal needle treatment. Drugs can be injected to the epidermal, the dermal, the subcutaneous fat, or the muscle tissues as well as to a blood vessel or another specific target organ in these tissues. In an exemplary embodiment of the invention, drug delivery system is disclosed. The needle system comprises a drug tank or a cocktail of drugs in a single tank or several separate tanks. The needle system implemented in accordance with the present invention described hereinabove. In a planned manner with a precise selected location and timing, a needle or plurality of needles are penetrating the skin and the drug is injected to the selected position, tissue or organ with the appropriate dose. The system can be attached and used repeatedly to provide drug delivery for longer periods, e.g., a week. The needle system can be used to deliver several drugs in a single system with accurate time correlation between the deliveries of each drug. Optionally, the needle system comprises several needles and each drug is delivered using a different needle. Additionally or alternatively, each drug is delivered to different position, tissue or organ. For example, a first drug is delivered by injection the drug into the epidermis then the first needle will penetrate to the epidermis, i.e., less than 1 mm deep. A second drug, composed of bigger molecules, need to be injected to the intercellular fluids, so a second needle will penetrate the skin until it pass the epidermis and reach a "wet tissue". Further more, a third drug may be injected directly into a blood vassal. In this case, a third needle will be targeted to bring the needle tip into the interior of a blood vassal. Additionally or alternatively, a measurement subsystem is integrated to set the dose dynamically based on a measured parameter. Optionally, needle system can deliver drug to specific blood vessel type and may distinct between veins, arteries and capillaries blood vessels.

An example for optimal tissue targeting drag delivery is vaccination or immunization. The optimal tissue for vaccination differ between vaccines but in general it is known that in many cases the optimal tissue is the epidermis that contains a high concentration of antibodies to combat pathogens. In this case the vaccine may be injected to the preferred tissue and spread it over larger area using multiple needle and if desired also spread the doze over several layers for better response and reduced vaccine side effects.

A problem the present drug delivery needle system can solve is complications involved with chemotherapy drug delivery. In this case, the drugs that are used are so strong and the continuous use of the same veins is so abused that a permanent damages is incurred to the used veins. Sometimes such damages to the veins disable further treatments. Using the presented needle system the dose may be spread between several smaller veins (using a plurality of needles simultaneously attached to these veins) to reduce the toxicity of the treatment to a specific vein.

In an exemplary embodiment of the invention, targeting is done to a plurality of blood vessels using a plurality of needles.

Furthermore, if the tumor is close to the skin, the needle system can find, through Doppler imaging, the blood vessels that are driving the blood to the tumor and inject the chemotherapy drugs directly to the blood stream of the tumor. This can decrease the dosage and make the chemotherapy more affective.

In an exemplary embodiment of the invention, targeting is done to one or more blood vessels carrying the blood to a specific destination, e.g. a tumor or infected organ.

Figure 11A:
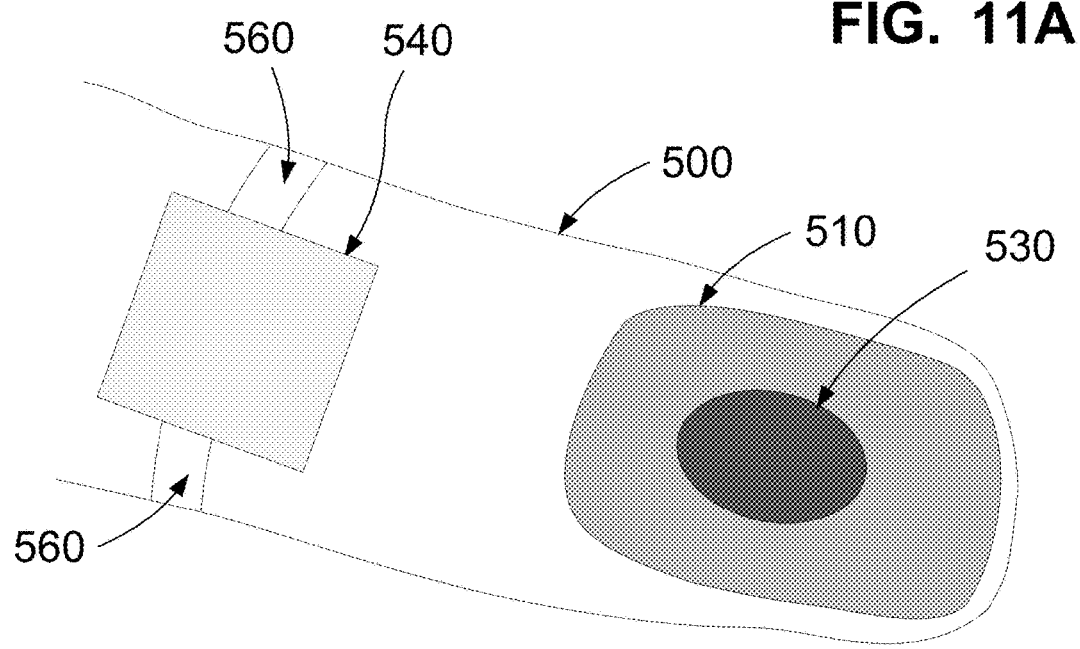
FIG. 11A-FIG. 11B are illustrations of a needle system to treat nail fungus by antifungal drug delivery to a nail artery.
Figure 11B:
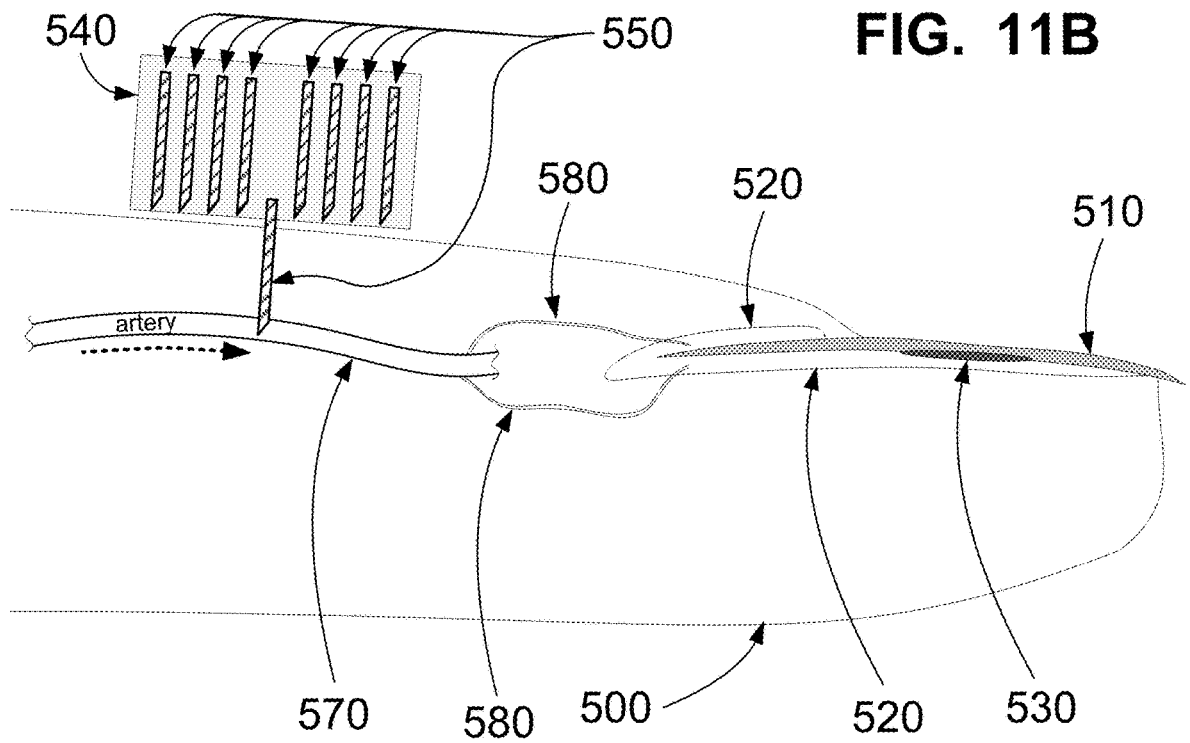

As another example, in an exemplary embodiment of the invention, a needle system to treat nail fungus with antifungal drugs is presented. The reference is made now to FIG. 11. FIG. 11 illustrates a needle system to treat nail fungus by antifungal drug delivery to a nail artery. FIG. 11A is a top view of a foot toe 500. FIG. 11B is a longitudinal cross section of the foot toe 500 across the foot toe nail 510. The nail is infected with fungus infection 530. The actual infection is below nail 510 and inside the bed nail tissue 520 (shown only on FIG. 11B). Nail fungus infections are very hard to access with drugs through the nail. The most effective and most used therapy for fungal nail infections are oral medication of anti-fungal drug such as Terbinafine. The drug reach the nail bed 320 through the blood stream. However, high dosage that spread and circulate all over the body is used. The drug is known to be toxic, especially for the liver, so long duration (months to years) low dosage treatment accompanied with a regular liver function blood test are needed. According to the present invention, a needle system medical device is used to treat the fungal infection 530. The needle system medical device 540 is attached to toe 500 using straps 560. The device 540 contains needles 550. The device take an image (as explained hereinbefore) and locate the artery 570 (or in the case of the foot toe, the two arteries) that supply the blood to toe nail bed 520. The blood supply to nail bed 520 comes from a plurality of capillaries 580 splits from artery 570. Treating nail fungal infection with device 540 allows an increased dosage of the antifungal drug directed mostly to the target toe nail bed 520 hence reduce the toxicity to the rest of the body thus increases treatment effectiveness and reduces the treatment duration.

In an exemplary embodiment of the invention, a needle system device is used for clinical trials. Since the dosage and the trimming are precisely met, the clinical trial results are much more reliable.

In an exemplary embodiment of the invention, a needle system device is used for Intravenous (IV) therapy. IV therapy include IF feeding, IV blood and liquid supplement and medication treatment such as chemotherapy.

Blood Tests

Another major exploit of hypodermal needle medical treatments is blood tests. In an exemplary embodiment of the invention, a device for painless and harmless blood extraction for performing blood analysis, or blood tests is disclosed. The device is strapped to a skin area used for blood taking, i.e., a skin area where blood veins are close enough to the skin, e.g., above the wrist or above the elbow. The needle system monitors, i.e., take ultrasound image or scan the skin area under the device. Using the image, optionally, with the aid of Doppler imaging, the needle system identifies a target blood vein and insert an appropriate needle, implemented in accordance with the present invention, to penetrate this blood vein, in order to extract the blood from this selected blood vein. Blood is taken out to a test tube from a blood port integrated into the device. Additionally or alternatively, blood measurements are done in the needle system device and the results are transmitted to the health care information system. Additionally or alternatively, the blood is stored in an integrated tube or tank inside the device and the device, after detached from the patient, is sent for further monitoring. Optionally, the integrated tube in the device has an optical transparent window allowing an optical blood test to be performed without taking the blood out from the tube in the device. Optionally, the device is disposable and disposed after the blood tests are performed.

Glucose Concentration Tests

In an exemplary embodiment of the invention, a glucose measurement device is provided. The glucose measurement device include an array of needles in accordance with the present invention, each needle is associated with a glucose measurement subsystem. Each time the controller selects to make a measurement, it instructs a needle to penetrate the skin to a proper depth and a glucose measurement is taken. The measurement can be transmitted via wireless link to the patient smart phone or patient monitoring device or to the health care information system. One needle system patch with plurality of needle may be used for taking glucose measurements for several days. The patient does not feel nor know when the measurement is taken. Measurements can be taken in predefined manner, e.g., morning, noun, evening, or in dynamic manner. For example, if there is a high level reading the measurements sampling rate may increases. Optionally, the measurement is initiated by the patient. Optionally, the needle system inject insulin to diabetic patient condition upon his blood glucose concentration measurements.

Fat Removal

In an exemplary embodiment of the invention, a fat removal device is presented. The fat removal device may be a patch that is placed in areas of excessive subcutaneous fat tissue. The patch contains an array of needles in accordance with the present invention. The needles penetrate the skin and reach the subcutaneous fat tissue. When the needles reach to the target tissue the suction subsystem sucks a portion of the fats or portion of the fat cells to a tank on the device. When the desired amount of fat had been suctioned the treatment ends and the patient remove the patch from skin and disposed it.

Acupuncture and Nerve System Treatments

In an exemplary embodiment of the invention, a nerve system treatment device is disclosed. The device contains an array of micro needle that are used to stimulate the human nerve system. This device is perform treatment that is similar to acupuncture treatment, i.e., to stimulate the nerve system for relaxing or therapeutic uses. More accurate targeting of nerve sensors can be performed by the needle system due to its needle movement accuracy and the imaging capabilities. Furthermore both vibration and electric stimuli through the needles can be achieved using needle system implemented in accordance with the present invention. The nerve stimulation may be done using vibration near the nerve sensor or via electric stimulus to the nerve sensor. Optionally or alternatively, the nerve stimulation may be done using material injection or local heating. The presented device is able to replace currently used Transcutaneous Electrical Nerve Stimulation (TENS) devices and Electrical Muscle Stimulation (EMS) devices with more accurate and better targeted stimulations.

In an exemplary embodiment of the invention, a needle system device moves a needle to target a nerve organ or fiber and the needle system stimulate the nerve organ or fiber with the aid of the needle. The stimuli is performed using electric stimuli, heat stimuli, material injection stimuli or needle vibration stimuli.

In an exemplary embodiment of the invention, a needle system device is used to treat neuropathic pains and other irritating nerve system sensations. The needle device allocates the target nerve fibers using its imaging capabilities and is performed one of or a combination of the following: (1) inject to the surrounding of the nerve fibers anesthetic drugs; (2) stimulate the nerve fibers to inhibit the sensation; (3) inject medication to cure or promote rehabilitation of the nerve fibers.

Skin Lesions Treatments

In an exemplary embodiment of the invention, a skin lesions remover device is disclosed. The device is attached over the lesion on the skin. The device scan the aera under the skin and analyze it. The device contains an array of needles in accordance to the present invention. The device, optionally analyzes the lesion using the needles. Analyzing contains measure of the properties of the lesion like its color, strength, structure and the like. The device measure the lesion 3D shape, depth and its boundaries with the benign tissue. After analysis the device kill the lesion by mechanically insertion and retracting the needles into the lesion or alternatively or optionally by electrical burning using the needles or optionally or alternatively by chemically or biologically materials injection into the lesion. The patch/device is placed on the lesion for several days. Optionally the device measure the effectiveness of the treatment. Optionally the device promote building of benign tissue in place of the lesion. When the device is removed, the lesion is totally disappeared and a healthy skin is grown instead.

In an exemplary embodiment of the invention, a needle system device is used to help surgeon to remove skin lesions completely using lesion coloring. Current protocol for removing lesions that are suspected to be malignant is removing the lesion and take the removed tissues to histological test under microscope. If the histological test indicate that not all the malignant lesion was removed, another pass of surgical removal is performed. This procedure can take several passes and few hours for each lesion.

Figure 12:
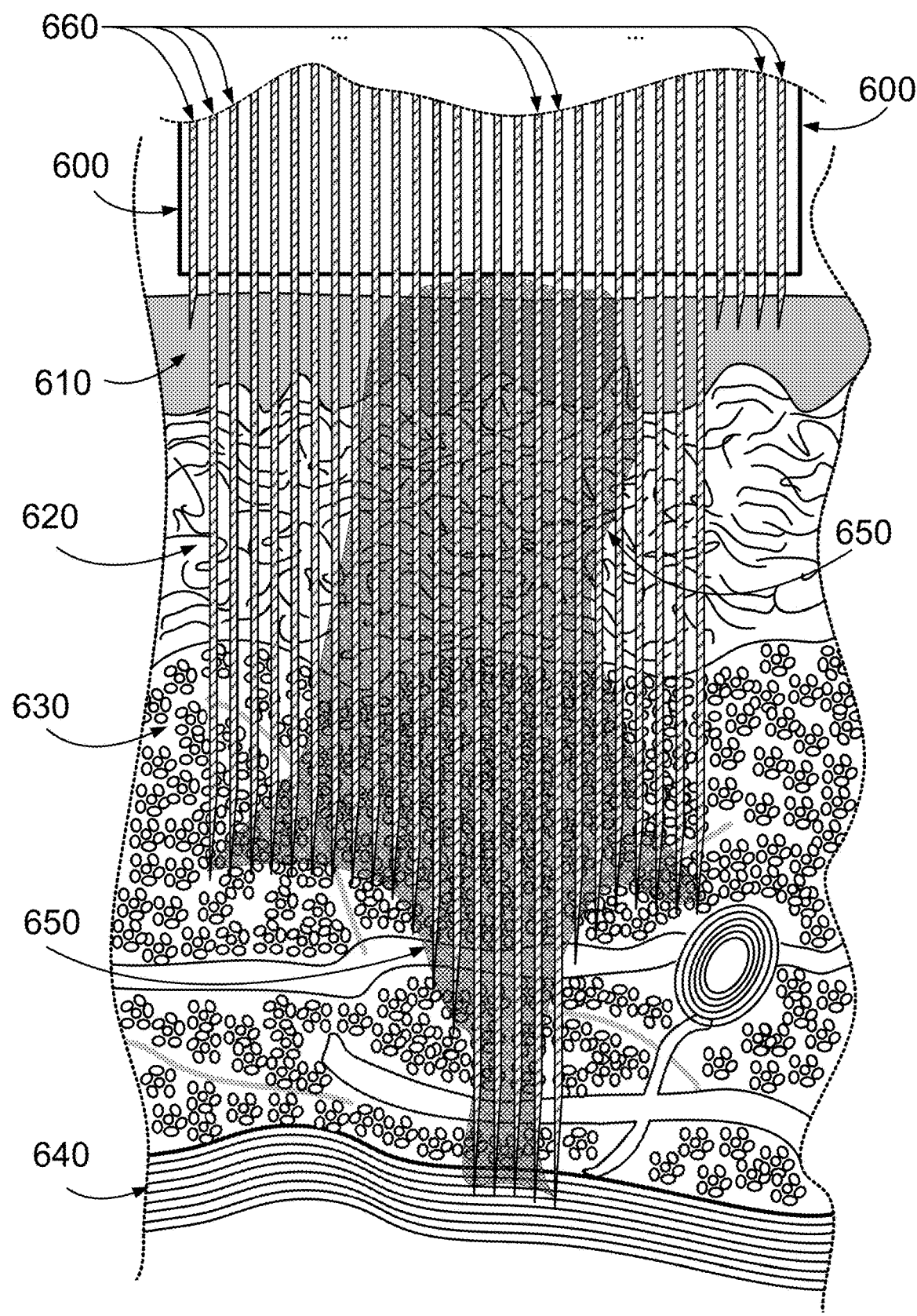
FIG. 12 is an illustration of a needle system for treatment of skin lesions.

Reference is now made to FIG. 12 illustrating a needle system for treatment of skin lesions. A needle system device 600 is attached to the skin over the lesion 650. In this exemplary illustration the lesion, probably malignant, is very deep and spread over the epidermis 610, the dermis 620, the subcutaneous fat tissue 630, and the top of the muscle tissue 640. Device 600 has an array of needles 660. After attachment of device 600, needles 660 are brought into contact with skin to perform ultrasound imaging of the area under device 600. With the aid of the ultrasound analysis the full 3D shape of the lesion is captured. Each needle 600 in the array, that has a portion of the lesion underneath it, is inserted to pass through the lesion and stop in benign tissue location deeper than the lesion. After all needle 600 are in their deepest position (this needle state illustrated in FIG. 12), the needles retracts back performing in all volume the lesion exist one or a combination of the following treatments: (1) burning or killing the lesion by heat, vibration, electricity or chemicals; (2) injecting medication or chemicals to the lesion volume; (3) coloring the lesion; and/or (4) extracting or sucking the lesion. When all needles 660 are back to the initial position the device is detached from the skin. Optionally, under round of treatment is performed. For example an injection of healing and rehabilitation medication can be used to encourage growth of benign tissues over the lesion volume. Optionally, the retraction of needle 660 is done in slow pace to allow small volume of regrowth of the benign tissue and regulate the regrowth for better healing and prevention of scares. In the case where the lesion is malignant and a surgery is the preferred mean to remove the lesion, the surgeon first use device 600 to color the lesion, then the surgeon remove the lesion according to the coloring of the lesion done by device 600. The removed lesion is then taken to histological test, however, the chances that the first cut removes all the lesion is much higher than the chance without the coloring with the device and surgery time is reduced dramatically. Moreover, the chance that unneeded benign tissues will be removed using this device aided coloring procedure is reduced.

The term skin lesion herein means warts, moles, acne, scares, wounds, sores, benign tumors, malignant tumors or any other skin diseases, anomalies or irregularities.

In an exemplary embodiment of the invention there is provided a method for hypodermic treatment that penetrate the skin with a plurality of needle that color, burn or destroy the complete volume of a lesion under the treated skin area.

Hair Removal and Hair Nurturing

In an exemplary embodiment of the invention, hair removal device is disclosed. The device is attached to a hairy skin area. The device contains an array of needle in accordance to the present invention. The device scans the locations of the hair papillae and targets a needle to each hair papilla. When the needle reaches the papilla it burns it by electric signal, vibration, or by chemical injection.

Hair Regrowth

Similar to the case of nail fungal infection, in order to combat hair dilution and to balding, medications like Minoxidil and Finasteride are used. Those medication are targeted to the hair papillae but circulate all over the body and create side effects. In an exemplary embodiment of the invention, hair regrowth device is disclosed. The device is attached to a skin area with diluted hair. The device contains an array of needle in accordance to the present invention. The device scans the locations of the hair papillae and targets a needle to each hair papilla. When the needle reaches the papilla it inject healing and regrowth medications such as Minoxidil or Finasteride or the like to the hair papillae area. Such a targeted treatment reduce dramatically the needed dosage and make the treatment shorter and more efficient Sweat Problems In an exemplary embodiment of the invention, over sweating (hyperhidrosis) treatment device is disclosed. The device is attached to a sweetening skin area. The device contains an array of needle in accordance to the present invention. The device scans the locations of the sweat glades and targets a needle to each sweat glade. When the needle reaches the sweat glade it burns it by electric signal, vibration, or by chemical injection.

Tattoo Paint and Removal

In an exemplary embodiment of the invention, tattoo printing device is disclosed. The device is attached to a skin area. The desired tattoo image is downloaded to the device. Each needle in the array is in charge of painting a single pixel in the tattoo image. The needle is loaded with the amount of ink (in color tattoo a mixture of colored ink) and inject the ink into the epidermis. This operation print a tattoo on the skin.

In an exemplary embodiment of the invention, tattoo removal device is disclosed. The device is attached to a skin area. The tattoo image and the device is scanned and where needed a needle inject tattoo removing material to the proper depth in the epidermis or alternatively the needle suck or remove some of the epidermal tissue that contains the tattoo ink.

Other Esthetic and Cosmetic Application

Similar to the technics described above, a needle system device may be used for skin anti-aging applications, skin peeling, scars illumination and skin tightening. In skin tightening application the needles are used to stretch excessive skin after massive weight loss or liposuction treatment. The needle system selectively destroys cells in such a way that the connectivity of the skin still remain but the skin surface size is reduced by tightly closing the practically planed gaps created by destroying the excessive cells in the skins tissues (both in the epidermis and dermis).

Non-Medical Applications

The following needle system is very precise and versatile. Due to the tightly integration with other capability offered by the semiconductor industry the present invention can be used for non medical applications as well. Those can be for sawing fabrics, precise fabrication of micro elements, R&D tools, lab equipment, etc.

In an exemplary embodiment of the invention the object that is treated by the needle system is an article of manufacturing and the needle system is used for manipulating or piercing the object during the process of the manufacturing.

In an exemplary embodiment of the invention the object that is treated by the needle system is a lab object under test or a biological organ and the system is used for testing or measuring or manipulating the lab object under test or the biological organ. It is expected that during the life of a patent maturing from this application many relevant applications will be developed and the scope of the implementation is intended to include all such new technologies a priori.

The terms "comprises", "comprising", "includes", "including", "having" and their conjugates mean "including but not limited to".

The term "consisting of means "including and limited to".

As used herein, the singular form "a", "an" and "the" include plural references unless the context clearly dictates otherwise. For example, the term "an element" or "at least one element" may include a plurality of elements, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An apparatus for piercing an object comprising:
(a) a semiconductor die;
(b) one or more needles; and (c) one or more actuators comprising a plurality of piezoelectric crystals that forms a plurality of arms that are configured to grip the one or more needles, wherein:
  (1) the needles and actuators are fabricated on the die;
  (2) the needles are configured to pierce the object;
  (3) the actuators are attached to the die substrate;
  (4) the piezoelectric crystals are configured to expand or contract;
  (5) the arms are configured to dynamically hold or release the grip from the needles by expanding or contracting some of the plurality of the piezoelectric crystals; and
  (6) when some of said arms hold the needles, these holding arms are configured to move the one or more needle relative to the die plane by expanding or contracting some of the plurality of the piezoelectric crystals.

2. A needle system comprising a controller and one or more apparatuses of claim 1.

3. A method for hypodermic treatment comprising the steps of:
  a) attaching to a skin the needle system of claim 2;
  b) penetrating the skin by moving the needles into the skin;
  c) performing by the needles an action comprising any one of or a combination of (1) injecting materials; (2) extracting materials; (3) stimulating organs or tissues; (4) burning or destructing organs or tissues;
  d) retracting the needles; and
  e) detaching the needle system.

4. The method of claim 3, wherein the method further comprising the step of imaging the area underneath the skin.

5. The method of claim 4, wherein, conditioned upon the imaging step, said one or more needles are targeted to any one of (1) a blood vessel; (2) nerve organ or fiber; (3) hair papilla; (4) sweat glade; and (5) lesion, identified in the image.

6. The method of claim 4, wherein, conditioned upon the imaging step, said one or more needles are targeted to any one of (1) dermis tissue; (2) epidermis tissue; (3) subcutaneous fat tissue; (4) muscle tissue; (5) boundaries between these tissues; and (6) intercellular fluid, that are identified by an image created in the imaging step.

7. The method of claim 4, wherein said step of imaging the area underneath the skin further comprising operating said needles in a division scheme where portion of the needles are transmitting ultrasound signals and another portion of the needles are receiving ultrasound signals.

8. The method needle system of claim 4, wherein said step of imaging the area underneath the skin further comprising successive image data capturing steps wherein in each said image data capturing step the needle tip locations are different.

9. The method of claim 4, wherein said step of imaging the area underneath the skin further comprising one or more image data capturing steps, wherein the image data is transferred from the needle system to a remote computing service and a processed image or a treatment instructions are transmitted back to the needle system.

10. The method of claim 3, wherein said needles are injecting ink to print a tattoo or extract ink from the skin to remove a tattoo.

11. The needle system of claim 2, wherein said one or more needles are configured to penetrate a human organ and the needle system is used for hypodermal treatment.

12. The needle system of claim 11, wherein said needle system is further configured to perform any one of or any combination of (1) drug delivery; (2) blood extraction; (3) blood analysis; (4) glucose measurements; (5) blood measurements; (6) nerve stimulation; (7) hair removal; (8) hair nurturing; (9) tattoo printing; (10) tattoo removal; (11) sweat glade destructing; and (12) skin lesions removal.

13. The needle system of claim 2, wherein said one or more needles are configured to penetrate an article of manufacturing and the system is used for manipulating or piercing the article of manufacturing during the process of the manufacturing.

14. The needle system of claim 2, wherein said one or more needles are configured to penetrate a lab object under test or a biological organ and the system is used for testing or measuring or manipulating the lab object under test or the biological organ.

15. The apparatus of claim 1, wherein said one or more needles are configured to slide over the die plane.

16. The apparatus of claim 1, wherein one or more said needles moves out of die plane.

17. The apparatus of claim 1, wherein said apparatus comprises actuator driver that drives electric signals to activate the one or more actuators.

18. The apparatus of claim 1, wherein said apparatus comprises power subsystem that provides energy to activate the one or more actuators.

19. The apparatus of claim 1, wherein said one or more needles are used as ultrasound transducers to generate an image of the object.

20. The apparatus of claim 1, wherein said needle has mechanical support to hold the needle and to allow sliding only to a desired direction.

* * * * *